US007393882B2

(12) United States Patent
Wu et al.

(10) Patent No.: US 7,393,882 B2
(45) Date of Patent: Jul. 1, 2008

(54) DENTAL PASTES, DENTAL ARTICLES, AND METHODS

(75) Inventors: Dong Wu, Woodbury, MN (US); Brant U. Kolb, Afton, MN (US); Sumita B. Mitra, West St. Paul, MN (US); Bradley D. Craig, Cottage Grove, MN (US); Brian N. Holmes, St. Paul, MN (US); Richard P. Rusin, Woodbury, MN (US); Mark S. Windisch, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 377 days.

(21) Appl. No.: 10/353,505

(22) Filed: Jan. 29, 2003

(65) Prior Publication Data

US 2003/0181541 A1 Sep. 25, 2003

Related U.S. Application Data

(60) Provisional application No. 60/353,593, filed on Jan. 31, 2002.

(51) Int. Cl.
*A61K 6/08* (2006.01)
*A61K 6/083* (2006.01)
*A61C 5/08* (2006.01)

(52) U.S. Cl. ............... 523/116; 523/118; 433/228.1
(58) Field of Classification Search ............... 523/116, 523/118; 433/228.1
See application file for complete search history.

(56) References Cited

U.S. PATENT DOCUMENTS

| | | | |
|---|---|---|---|
| 2,984,628 A | 5/1961 | Alexander et al. |
| 3,018,262 A | 1/1962 | Schroeder |
| 3,066,112 A | 11/1962 | Bowen |
| 3,117,099 A | 1/1964 | Proops et al. |
| 3,179,623 A | 4/1965 | Bowen |
| 3,194,784 A | 7/1965 | Bowen |
| 3,442,817 A | 5/1969 | Luebke |
| 3,514,252 A | 5/1970 | Levy, Jr. et al. |
| 3,539,533 A | 11/1970 | Lee, II et al. |
| 3,629,187 A | 12/1971 | Waller |
| 3,708,296 A | 1/1973 | Schlesinger |
| 3,709,706 A | 1/1973 | Sowman |
| 3,709,866 A | 1/1973 | Waller |
| 3,729,313 A | 4/1973 | Smith |
| 3,741,769 A | 6/1973 | Smith |
| 3,751,399 A | 8/1973 | Lee et al. |
| 3,766,132 A | 10/1973 | Lee et al. |
| 3,808,006 A | 4/1974 | Smith |
| 3,860,556 A | 1/1975 | Taylor |
| 3,926,906 A | 12/1975 | Lee, II et al. |
| 4,002,669 A | 1/1977 | Gross et al. |
| 4,069,055 A | 1/1978 | Crivello |
| 4,071,424 A | 1/1978 | Dart et al. |
| 4,115,346 A | 9/1978 | Gross et al. |
| 4,150,012 A | 4/1979 | Joos |
| 4,216,288 A | 8/1980 | Crivello |
| 4,250,053 A | 2/1981 | Smith |
| 4,250,311 A | 2/1981 | Crivello |
| 4,259,117 A | 3/1981 | Yamauchi et al. |
| 4,292,029 A | 9/1981 | Craig et al. |
| 4,308,190 A | 12/1981 | Walkowiak et al. |
| 4,327,014 A | 4/1982 | Kawahara et al. |
| 4,374,937 A | 2/1983 | Nemcek et al. |
| 4,379,695 A | 4/1983 | Orlowski et al. |
| 4,387,240 A | 6/1983 | Berg |
| 4,389,497 A | 6/1983 | Schmitt et al. |
| 4,394,403 A | 7/1983 | Smith |
| 4,404,150 A | 9/1983 | Tsunekawa et al. |
| 4,427,799 A | 1/1984 | Orlowski et al. |
| 4,427,823 A | 1/1984 | Inagaki et al. |
| 4,442,240 A | 4/1984 | Suh |
| 4,491,508 A | 1/1985 | Olson et al. |
| 4,503,169 A | 3/1985 | Randklev |
| 4,512,743 A | 4/1985 | Santucci et al. |
| 4,544,359 A | 10/1985 | Waknine |
| 4,545,924 A | 10/1985 | Ritter, II |
| 4,547,531 A | 10/1985 | Waknine |
| 4,552,906 A | 11/1985 | Podszun et al. |
| 4,612,138 A | 9/1986 | Keiser |

(Continued)

FOREIGN PATENT DOCUMENTS

CA        2074128        1/1993

(Continued)

OTHER PUBLICATIONS

ASTM D 523-89 (Reapproved 1994), "Standard Test Method for Specular Gloss," *Annual Book of ASTM Standards*, vol. 06.01, pp. 36-40 (Mar. 31, 1989).

(Continued)

*Primary Examiner*—Tae H Yoon
(74) *Attorney, Agent, or Firm*—Sean J. Edman

(57) ABSTRACT

The present invention provides a dental paste, a dental article, methods of making and using the dental paste, and compositions prepared therefrom. In one embodiment, the dental paste includes (a) a filler including porous, non-pyrogenic silica having a silane treated surface and being substantially free of heavy metals and (b) a filler including non-aggregated primary silica particles, with the fillers being dispersed in a hardenable resin.

23 Claims, No Drawings

U.S. PATENT DOCUMENTS

| | | | |
|---|---|---|---|
| 4,617,327 A | 10/1986 | Podszun | |
| 4,619,817 A | 10/1986 | Stambaugh et al. | |
| 4,629,746 A | 12/1986 | Michl et al. | |
| 4,642,126 A | 2/1987 | Zador et al. | |
| 4,649,165 A | 3/1987 | Kuhlmann | |
| 4,652,274 A | 3/1987 | Boettcher et al. | |
| 4,661,540 A | 4/1987 | Le et al. | |
| 4,696,955 A | 9/1987 | Kuhlmann | |
| 4,707,504 A | 11/1987 | Walkowiak et al. | |
| 4,719,091 A | 1/1988 | Wusirika | |
| 4,737,593 A | 4/1988 | Ellrich et al. | |
| 4,746,685 A | 5/1988 | Masuhara et al. | |
| 4,769,351 A | 9/1988 | Soumiya et al. | |
| 4,772,511 A | 9/1988 | Wood et al. | |
| 4,772,530 A | 9/1988 | Gottschalk et al. | |
| 4,778,671 A | 10/1988 | Wusirika | |
| 4,784,794 A | 11/1988 | Kato | |
| 4,792,577 A | 12/1988 | Chen et al. | |
| 4,859,716 A | 8/1989 | Ibsen et al. | |
| 4,868,288 A | 9/1989 | Meier | |
| 4,874,450 A | 10/1989 | Gottschalk | |
| 4,885,332 A | 12/1989 | Bilkadi | |
| 4,886,624 A | 12/1989 | Gradeff et al. | |
| 4,923,905 A | 5/1990 | Masuhara et al. | |
| 4,927,560 A | 5/1990 | Osaka et al. | |
| 4,931,414 A | 6/1990 | Wood et al. | |
| 4,933,202 A | 6/1990 | Rheinberger et al. | |
| 4,946,665 A | 8/1990 | Recasens et al. | |
| 4,954,414 A | 9/1990 | Adair et al. | |
| 4,985,229 A | 1/1991 | Obitsu et al. | |
| 4,985,340 A | 1/1991 | Palazzotto et al. | |
| 5,037,579 A | 8/1991 | Matchett | |
| 5,055,372 A | 10/1991 | Shanklin et al. | |
| 5,057,393 A | 10/1991 | Shanklin et al. | |
| 5,073,476 A | 12/1991 | Meier et al. | |
| 5,084,586 A | 1/1992 | Farooq | |
| 5,089,536 A | 2/1992 | Palazzotto | |
| 5,124,417 A | 6/1992 | Farooq | |
| 5,126,394 A | 6/1992 | Revis et al. | |
| 5,132,337 A | 7/1992 | Panster et al. | |
| 5,137,448 A | 8/1992 | Dougherty et al. | |
| 5,177,120 A | 1/1993 | Hare et al. | |
| 5,190,583 A | 3/1993 | Menzel et al. | |
| 5,192,815 A | 3/1993 | Okada et al. | |
| 5,219,899 A | 6/1993 | Panster et al. | |
| 5,234,870 A | 8/1993 | Osaka et al. | |
| 5,248,706 A | 9/1993 | Panster et al. | |
| 5,275,759 A | 1/1994 | Osaka et al. | |
| 5,276,068 A | 1/1994 | Waknine | |
| 5,318,999 A | 6/1994 | Mitra et al. | |
| 5,332,429 A | 7/1994 | Mitra et al. | |
| 5,332,779 A | 7/1994 | Mohri et al. | |
| 5,350,782 A | 9/1994 | Sasaki et al. | |
| 5,401,528 A | 3/1995 | Schmidt | |
| 5,444,104 A | 8/1995 | Waknine | |
| 5,449,703 A | 9/1995 | Mitra et al. | |
| 5,460,701 A | 10/1995 | Parker et al. | |
| 5,470,910 A | 11/1995 | Spanhel et al. | |
| 5,502,087 A | 3/1996 | Tateosian et al. | |
| 5,545,676 A | 8/1996 | Palazzotto et al. | |
| 5,558,849 A | 9/1996 | Sharp | |
| 5,593,781 A | 1/1997 | Nass et al. | |
| 5,609,675 A | 3/1997 | Noritake et al. | |
| 5,643,497 A | 7/1997 | Kaga et al. | |
| 5,648,407 A | 7/1997 | Goetz et al. | |
| 5,658,376 A | 8/1997 | Noguchi et al. | |
| 5,694,701 A | 12/1997 | Huelsman et al. | |
| 5,698,483 A | 12/1997 | Ong et al. | |
| 5,760,126 A | 6/1998 | Engle et al. | |
| 5,776,239 A | 7/1998 | Bruno | |
| 5,830,242 A | 11/1998 | Yao | |
| 5,856,373 A | 1/1999 | Kaisaki et al. | |
| 5,879,715 A | 3/1999 | Higgins et al. | |
| 5,886,069 A | 3/1999 | Bolt | |
| 5,935,275 A | 8/1999 | Burgard et al. | |
| 5,936,006 A | 8/1999 | Rheinberger et al. | |
| 5,942,559 A | 8/1999 | Voser et al. | |
| 5,980,697 A | 11/1999 | Kolb et al. | |
| 5,985,168 A | 11/1999 | Phule | |
| 5,998,495 A | 12/1999 | Oxman et al. | |
| 6,020,528 A | 2/2000 | Leppard et al. | |
| 6,025,406 A | 2/2000 | Oxman et al. | |
| 6,030,606 A | 2/2000 | Holmes | |
| 6,063,830 A | 5/2000 | Deguchi et al. | |
| 6,136,886 A | 10/2000 | Deguchi | |
| 6,245,872 B1 | 6/2001 | Frey et al. | |
| 6,302,926 B1 | 10/2001 | Anselmann et al. | |
| 6,306,926 B1 | 10/2001 | Bretscher et al. | |
| 6,376,590 B2 | 4/2002 | Kolb et al. | |
| 6,387,981 B1 | 5/2002 | Zhang et al. | |
| 6,399,037 B1 | 6/2002 | Pflug et al. | |
| 6,417,246 B1 | 7/2002 | Jia et al. | |
| 6,572,693 B1 | 6/2003 | Wu et al. | |
| 6,680,013 B1 * | 1/2004 | Stein et al. | 264/44 |
| 7,156,911 B2 * | 1/2007 | Kangas et al. | 106/35 |
| 2002/0022677 A1 | 2/2002 | Teramae et al. | |
| 2002/0156152 A1 | 10/2002 | Zhang et al. | |

FOREIGN PATENT DOCUMENTS

| | | |
|---|---|---|
| CA | 2202732 | 10/1997 |
| DE | 693 14 374 T2 | 10/1993 |
| DE | 195 24 362 A1 | 1/1996 |
| DE | 195 08 586 C2 | 9/1996 |
| DE | 195 40 623 A1 | 5/1997 |
| EP | 0 173 567 A2 | 3/1986 |
| EP | 0 184 467 A2 | 6/1986 |
| EP | 0 094 914 B1 | 9/1986 |
| EP | 0 315 186 A2 | 5/1989 |
| EP | 0 315 186 A3 | 5/1989 |
| EP | 0 368 657 A2 | 5/1990 |
| EP | 0 368 657 A3 | 5/1990 |
| EP | 0 434 334 A1 | 6/1991 |
| EP | 0 523 545 A1 | 1/1993 |
| EP | 0 530 926 | 3/1993 |
| EP | 0 315 186 B1 | 4/1993 |
| EP | 0 368 657 B1 | 8/1993 |
| EP | 0 565 403 A1 | 10/1993 |
| EP | 0 434 334 B1 | 2/1994 |
| EP | 0 523 545 B1 | 8/1995 |
| EP | 0 530 926 B1 | 4/1996 |
| EP | 0 712 912 A2 | 5/1996 |
| EP | 0 732 099 | 9/1996 |
| EP | 0 565 403 B1 | 10/1997 |
| EP | 0 841 304 A1 | 5/1998 |
| EP | 1 149 573 A2 | 10/2001 |
| EP | 1 149 573 A3 | 10/2001 |
| GB | 1596241 | 8/1981 |
| GB | 2310855 | 9/1997 |
| JP | 58079818 A | 5/1983 |
| JP | 58135131 A | 8/1983 |
| JP | 3-46407 | 6/1984 |
| JP | 59107969 A | 6/1984 |
| JP | 60103033 A | 6/1985 |
| JP | 60137827 A | 7/1985 |
| JP | 4-72768 | 9/1985 |
| JP | 60176920 A | 9/1985 |
| JP | 60255622 A | 12/1985 |
| JP | 61141620 A | 6/1986 |
| JP | 61227917 A | 10/1986 |
| JP | 61270217 A | 11/1986 |
| JP | 62065932 A | 3/1987 |
| JP | 62091421 A | 4/1987 |
| JP | 62128924 A | 6/1987 |

| | | |
|---|---|---|
| JP | 1076919 A | 9/1987 |
| JP | 1079015 A | 9/1987 |
| JP | 1083518 A | 9/1987 |
| JP | 62212224 A | 9/1987 |
| JP | 62226815 A | 10/1987 |
| JP | 63002809 A | 1/1988 |
| JP | 1083519 A | 3/1989 |
| JP | 1083520 A | 3/1989 |
| JP | 1176225 A | 7/1989 |
| JP | 2137729 A | 5/1990 |
| JP | 2137730 A | 5/1990 |
| JP | 2137731 A | 5/1990 |
| JP | 2137732 A | 5/1990 |
| JP | 3174326 A | 7/1991 |
| JP | 4031307 A | 2/1992 |
| JP | 4089319 A | 3/1992 |
| JP | 6-191827 | 7/1994 |
| JP | 7-17820 | 1/1995 |
| JP | 7118016 A | 5/1995 |
| JP | 7-291817 | 11/1995 |
| JP | 8277114 A | 1/1996 |
| JP | 8-311115 | 11/1996 |
| JP | 9-194674 | 7/1997 |
| JP | 9235119 A | 9/1997 |
| WO | WO93/05875 A1 | 4/1993 |
| WO | WO96/34829 A1 | 11/1996 |
| WO | WO98/13008 A1 | 4/1998 |
| WO | WO99/17716 A1 | 4/1999 |
| WO | WO99/65453 A1 | 12/1999 |
| WO | WO 00/03688 A1 | 1/2000 |
| WO | WO 00/20494 A1 | 4/2000 |
| WO | WO 00-25729 | 5/2000 |
| WO | WO 01/30304 | 5/2001 |
| WO | WO 01/30306 A1 | 5/2001 |
| WO | WO 01/30307 | 5/2001 |

OTHER PUBLICATIONS

ASTM-D2805-95, "Standard Test Method for Hiding Power of Paints by Reflectometry," *Annual Book of ASTM Standards*, vol. 06.01, pp. 307-312 (Feb. 15, 1995).

Blumenthal, *The Chemical Behavior of Zirconium*, D. Van Nostrand Company, Princeton, NJ, pp. 311-338.

Burgard et al., "Routes to Deagglomerated Nanopowder By Chemical Synthesis," *Mat. Res. Soc. Symp. Proc.*, vol. 346, 1994, pp. 101-107.

Burgard, et al., "Synthesis and Colloidal Processing of Nanocrystalline ($Y_2O_3$-Stabilized) $ZrO_2$ Powders by a Surface Free Energy Controlled Process," *Mat. Res. Soc. Symp. Proc.*, vol. 432, 1997, pp. 113-112.

Cabot Corporation product brochure, "Cab-O-Sil® Untreated Fumed Silica Properties and Functions," 1978. Title Page, Publication page, and pp. 3-5.

Chang et al., "Optical properties of dense and porous spheroids consisting of primary silica nanoparticles," *Aerosol Science*, vol. 33, pp. 1701-1720 (2002).

Chatry et al., "The Role of Complexing Ligands in the Formation of Non-Aggregated Nanoparticles of Zirconia," *Journal of Sol-Gel Science and Technology*, vol. 1, 1994, pp. 233-240.

Chung et al. "Influence of manufacturing variables on surface properties and dynamic adsorption properties of silica gels," *Journal of Non-Crystalline Solids*, vol. 279, pp. 145-153 (2001).

Craig, *Restorative Dental Materials*, 8th Ed., 1989, pp. 256-257 only.

Decker, "Photoinitiated Curing of Multifunctional Monomers," *Chimia*, vol. 47, pp. 378-382 (1993).

Definition of "binary compound," Oct. 9, 1997 Retrieved from the On-line Medical Dictionary on Jun. 6, 2002 at <http://cancerweb.ncl.ac.uk./cgi-bin/omd?binary +compound> 1 pg.

Definition of "oxide," Oct. 9, 1997 Retrieved from the On-line Medical Dictionary on Jun. 6, 2002 at <http://cancerweb.ncl.ac.uk/cgi-bin/omd?oxide> 1 pg.

Degussa AG Product Brochure, "Technical Bulletin Pigments, AEROSIL® as a Thickening Agent for Liquid Systems, No. 23," Jul. 1989; Title page, Publication page, and pp. 3 and 29.

Degussa AG Product Brochure, "Technical Bulletin Pigments, AEROSIL® in Pharmaceuticals and Cosmetics, No. 49," Sep. 1997; Title page, Publication page, and pp. 5-6.

Grant, *Grant and Hackh's Chemical Dictionary*, 5th Edition, Title page, publication page, and pp. 106 and 231 (1987).

*Kirk-Othmer Concise Encyclopedia of Chemical Technology*, John Wiley & Sons, New York, Title page, Publication page, and pp. 1053-1057 (1985).

*Kirk-Othmer Encyclopedia of Chemical Technology*, 4th Ed., vol. 21, Title page, Publication page, and pp. 977-1032 (1977).

Lee et al., Handbook of Epoxy Resins, McGraw-Hill Book Co., New York 1967; Cover page, Title page, Preface, Glossary of Abbreviations, and Table of Contents only.

Macosko, Ed., *Rheology Principles, Measurements, and Applications*, VCH Publishers, Inc., New York, Title page and pp. 92-98 (1994).

Matijevic, Ed., *Surface & Colloid Science*, vol. 6, Wiley Interscience, 1973: Title page and pp. 23-30.

"Perthometer, Surface Texture Parameters," Mahr GMB, Gottingen, Germany ed. Sep. 1, 1999, 19 pgs.

Product Information Sheet, "Nalco Collodial Silica Product Line," 1 pg. (no date available).

Watts et al., "Determination of Polymerization Shrinkage Kinetics in Visible-Light-Cured Materials: Methods of Development," *Dental Materials*, Oct. 1991; pp. 281-287.

Kagaku Kogyo Nippousya, "12695 Chemical Commericial Goods," The Chemical Daily Co., Ltd., p. 217-220/E, 1E, (1995).

* cited by examiner

DENTAL PASTES, DENTAL ARTICLES, AND METHODS

This application claims the benefit of the U.S. Provisional Application Ser. No. 60/353,593, filed Jan. 31, 2002, which is incorporated herein by reference in its entirety.

BACKGROUND

Dental materials have special requirements. For health reasons, dental materials should be suitable for use in the oral environment. In certain applications, strength and durability of a dental material is important to ensure satisfactory performance. For example, for dental work at locations where mastication forces are generally great, high strength and durability is desirable. In other applications, an aesthetic character (e.g., luster and translucency) is desired. This is often the case where dental work is performed at locations where a tooth repair or restoration can be seen from a relatively short distance.

Strength in a dental material is typically achieved by adding fillers. Generally, a dental material has greater mechanical strength when it contains fillers having an average particle size greater than about 0.6 micrometers. A disadvantage of composites with such average particle size is that with repeated toothbrushing (a requirement for oral hygiene), the hardened resin can wear away leaving a dull, unaesthetic surface. The worn surface can be a site for subsequent plaque accumulation.

The use of fillers having an average particle size greater than about 0.6 micrometers also tends to result in dental materials that lack luster and aesthetic character. The matching of refractive indices of the components has been suggested as an approach to improve the visual opacity, and hence the aesthetic character, of such dental materials. However, such an approach restricts the latitude in formulating dental materials by limiting the selection of materials that may be used in the dental materials to those with matching refractive indices.

The use of smaller particles to improve the aesthetic qualities of dental materials is known in the dental arts. For example, dental pastes including non-aggregated silica particles having an average particle size of less than about 200 nanometers have been reported. However, when the loading levels of such fillers are increased to provide the desired mechanical strength upon hardening (e.g., at least about 70% by weight filler in the paste), the resulting pastes are generally sticky. The resulting stickiness of such dental pastes is undesirable for dental practice.

The use of a combination of different average particle size fillers in dental materials has also been disclosed. However, such combinations generally result in dental materials that are lacking in one or more desirable properties. For example, some combinations of different average particle size fillers cannot be loaded into a hardenable resin at high enough concentration to provide dental pastes that have desirable properties, such as mechanical strength upon curing. Other combinations of different average particle size fillers may provide adequate mechanical strength upon curing, but lack desirable aesthetic qualities.

Thus, there is a need in the art for dental pastes that provide a balance of desirable properties.

SUMMARY

In one aspect, the present invention provides a dental paste and articles prepared therefrom. The dental paste includes a hardenable resin; a first filler dispersed in the resin, the first filler including porous, non-pyrogenic silica having a silane treated surface and being substantially free of heavy metals; and a second filler dispersed in the resin, the second filler including non-aggregated primary silica particles having a silane treated surface and having an average diameter of at most about 200 nanometers, wherein the paste includes at least about 55% by weight of the combined first and second fillers based on the total weight of the paste. Preferably, the paste is substantially non-sticky, and more preferably has a SWD/Hardness value of at most about 0.5.

The present invention provides dental pastes that are useful for forming dental materials including, for example, dental restoratives, dental adhesives, casting materials, dental cements, dental sealants, and dental coatings. Preferably the dental paste, upon hardening, has one or more properties including, for example, a contrast ratio of at most about 50, a MacBeth value of at most about 0.4, a volumetric shrinkage of at most about 4%, a diametral tensile strength of at least about 15 MPa, a compressive strength of at least about 35 MPa, and a loss in polish of at most about 30% after 500 brushes in a polish retention test. Preferably the dental paste, upon hardening, forms a dental article. Preferred dental articles include, for example, dental mill blanks, dental prostheses, orthodontic devices, artificial crowns, anterior fillings, posterior fillings, and cavity liners.

In another aspect, the present invention provides a method of preparing a dental paste including dispersing in a hardenable resin a first filler including porous, non-pyrogenic silica having a silane treated surface and being substantially free of heavy metals; and dispersing in the hardenable resin a second filler including non-aggregated primary silica particles having a silane treated surface and having an average particle size of at most about 200 nanometers to form a paste, wherein the paste includes at least about 55% by weight of the combined first and second fillers.

In another aspect, the present invention provides a dental paste including a hardenable resin; a filler dispersed in the hardenable resin, the filler including porous, non-pyrogenic silica including aggregates of primary silica particles having an average particle size of about 20 nanometers to about 120 nanometers, wherein the filler has a bulk density of at least about 0.4 g/cm$^3$ and a surface area of at most about 150 m$^2$/g, the average size of the aggregated silica in the filler is about 1 micrometer to about 20 micrometers, and the silica is substantially free of heavy metals. Preferably the porous, non-pyrogenic silica includes a silane treated surface.

In another aspect, the present invention provides a method of preparing a filler in a dry powder form including drying a silica sol, the silica sol including primary silica particles having an average particle size of about 20 nanometers to about 120 nanometers dispersed in a volatile liquid, to form porous, non-pyrogenic silica including aggregates of primary silica particles, wherein the aggregated silica has an average aggregate size of about 1 micrometer to about 20 micrometers, the silica being substantially free of heavy metals; dispersing the silica in a volatile liquid to form a volatile liquid dispersion of porous, non-pyrogenic silica; treating the surface of the porous, non-pyrogenic silica dispersed in the volatile liquid with a silane to form a volatile liquid dispersion of porous, non-pyrogenic silica having a silane treated surface; and drying the volatile liquid dispersion to form the filler.

Optionally, the method includes calcining the silica at a temperature of at most about 650° C. Optionally, the filler may be dispersed in a hardenable resin to form a dental paste.

Definitions

As used herein, the term "paste" refers to a soft, viscous mass of solids dispersed in a liquid.

As used herein, the term "silica" refers to the compound silicon dioxide. See Kirk-Othmer Encyclopedia of Chemical Technology, 4th Ed., Vol. 21, pp. 977-1032 (1977).

As used herein, the terms "primary silica particles" or "ultimate silica particles" are used interchangeably and refer to the smallest unit particle used to build a larger structure, a three-dimensional network, a silica cluster, or a silica particle. Primary or ultimate silica particles are typically fully densified.

As used herein, the term "amorphous silica" refers to silica that does not have a crystalline structure as defined by x-ray diffraction measurements. Examples of amorphous silica include silica sols, silica gels, precipitated silica, and pyrogenic silica.

As used herein, the terms "porous silica" refers to a three-dimensional network of silica that has porosity. As such, a linear chain of silica particles would not have porosity. Porous silicas may be composed of aggregates of primary silica particles. Examples of porous silica include fumed silica, precipitated silica, silica gel, and silica clusters as described herein.

As used herein, the term "silica sol" refers to a stable dispersion of discrete, amorphous silica particles in a liquid, typically water.

As used herein, the terms "pyrogenic silica" and "fumed silica" are used interchangeably and refer to amorphous silicas formed in the vapor phase. Pyrogenic silica may contain, for example, a few hundred primary particles fused into branched-chain, three-dimensional aggregates. Examples of pyrogenic silica include products available under the trade designations AEROSIL OX-50, AEROSIL-130, AEROSIL-150, and AEROSIL-200 available from DeGussa AG, (Hanau, Germany) and CAB-O-SIL M5 available from Cabot Corp (Tuscola, Ill.).

As used herein, "non-pyrogenic silica" refers to amorphous silica that is not formed in the vapor phase. Examples of non-pyrogenic silicas include precipitated silicas, silica gels, and silica clusters as described herein.

As used herein, the term "silica gel" refers to three-dimensional networks of silica particles of colloidal dimensions (e.g., no greater than about 120 nanometers). Silica gels are porous silica and are typically manufactured by the gellation of relatively concentrated solutions of sodium silicate or salt-free colloidal silica, although silica gels may also be prepared by the hydrolysis and polycondensation of silicon alkoxides. Examples of silica gels include those available from Sigma-Aldrich (St. Louis, Mo.) and AnalytiChem Corporation (Harbor City, Calif.).

As used herein, the term "precipitated silica" refers to aggregates of primary silica particles of colloidal dimensions (e.g., no greater than about 120 nanometers). Precipitated silicas are typically powders obtained by coagulation of silica particles from an aqueous medium under the influence of high salt concentrations or other coagulants. Under typical conditions, the primary particles grow to sizes larger than 4-5 nanometers and are coagulated into aggregates. The entire liquid phase is not enclosed by the solid silica phase in contrast to the preparation of silica gel. Examples of precipitated silicas include those available under the trade designation ACEMATT HK-460 from Degussa AF, Germany.

As used herein, the term "substantially spherical" silica clusters refers to the general shape of the silica clusters. Substantially spherical silica clusters have an average aspect ratio of at most about 4:1, preferably at most about 3:1, more preferably at most about 2:1, and even more preferably at most about 1.5:1.

As used herein, the term "acicular" aggregates refers to the general shape of the aggregates (e.g., narrow and long, needle-like). Acicular aggregates preferably have an aspect ratio of greater than about 5:1, more preferably greater than about 6:1, and most preferably greater than about 7:1. Examples of acicular aggregates include, for example, fumed silica, which includes a fused, branched-chain, three-dimensional structure.

As used herein, "bulk density" refers to the weight per unit volume of a material. Bulk density for powders, as used herein, refers to the weight per unit volume of the neat, dry powder in a naturally packed state. Bulk density may provide a gross measure of powder properties including, for example, average particle size, particle size distribution, and morphology of the aggregates. A procedure for determining bulk density is included in the present application.

As used herein, "silane treated" means that the surface of a particle has been modified by application of a silane. Optionally, the silane may be a coupling agent that includes a reactive functionality (e.g., γ-methacryloxypropyltrimethoxysilane, A174).

As used herein, "dry powder" means a solid powder substantially free of volatile liquid. For example, a dry powder preferably includes at most about 5% by weight volatile liquid, more preferably at most about 2% by weight volatile liquid, and most preferably at most about 1% by weight volatile liquid.

As used herein, "filler" means a particulate material (e.g., an inorganic oxide) in dry powder form capable of being dispersed in a resin. For example, a dental composite preferably includes a filler dispersed in a resin.

As used herein, "SWD/Hardness" (the ratio of string work done to hardness) is a measurement of the stickiness of a composition. Specifically, a texture analyzer (e.g., from Examples, Test Methods section) can be used to determine SWD/Hardness values with lower values indicative of a less sticky composition.

As used herein, "hardenable" is descriptive of a material that can be cured or solidified e.g., by heating to remove solvent, heating to cause polymerization, chemical crosslinking, radiation-induced polymerization or crosslinking, or the like.

As used herein, "dispersed within a resin" means that a filler is mixed with a resin so that primary particles, three-dimensional networks of particles, and/or clusters are substantially separated in the resin.

As used herein, "agglomerated" is descriptive of a weak association of primary particles usually held together by charge or polarity. Agglomerated particles can typically be broken down into smaller entities by, for example, shearing forces encountered during dispersion of the agglomerated particles in a liquid.

In general, "aggregated" and "aggregates" are descriptive of a strong association of primary particles often bound together by, for example, residual chemical treatment, covalent chemical bonds, or ionic chemical bonds. Further breakdown of the aggregates into smaller entities is very difficult to achieve. Typically, aggregated particles are not broken down into smaller entities by, for example, shearing forces encountered during dispersion of the aggregated particles in a liquid.

As used herein, "aggregated silica" is descriptive of an association of primary silica particles often bound together by, for example, residual chemical treatment, covalent chemical bonds, or ionic chemical bonds. Although complete breakdown of aggregated silica into smaller entities may be difficult to achieve, limited or incomplete breakdown may be observed under conditions including, for example, shearing forces encountered during dispersion of the aggregated silica in a liquid. As used herein, a "silica cluster" refers to aggregated silica in which a substantial amount of the aggregated primary silica particles are loosely bound. "Loosely bound" refers to the nature of the association among the particles present in the silica cluster. Typically, the particles are associated by relatively weak intermolecular forces that cause the particles to clump together. Preferably, many of the silica clusters remain intact during dispersion into a hardenable resin for a dental material, even though some silica clusters may be fractured into smaller structures during the dispersion process. Thus, silica clusters are typically referred to as "loosely bound aggregated silica." The silica clusters disclosed in the present application are preferably substantially spherical and preferably not fully densified. The term "fully dense," as used herein, is descriptive of a particle that is near theoretical density, having substantially no open porosity detectable by standard analytical techniques such as the B.E.T. nitrogen technique (based upon adsorption of $N_2$ molecules from a gas with which a specimen is contacted). Such measurements yield data on the surface area per unit weight of a sample (e.g. $m^2/g$), which can be compared to the surface area per unit weight for a mass of perfect microspheres of the same size to detect open porosity. The term "not fully densified" as used herein, is descriptive of a particle that is less than theoretical density, and therefore, has open porosity. For such porous particles (e.g., clusters of primary particles), the measured surface area is greater than the surface area calculated for solid particles of the same size. Such measurements may be made on a Quantasorb apparatus made by Quantachrome Corporation of Syossett, N.Y. Density measurements may be made using an air, helium or water pycnometer.

As used herein, "particle size" refers to the longest dimension (e.g., diameter) of a particle.

As used herein, "substantially free of heavy metal" means that the silica clusters contain at most about 20% by weight heavy metal, preferably at most about 10% by weight heavy metal, and most preferably at most about 5% by weight heavy metal. As used herein, a "heavy metal" is a metal having an atomic number greater than about 28, and preferably greater than about 30.

As discussed more fully herein below, silica clusters disclosed in the present application are often manufactured in a process that includes drying and optionally heat treating and/or calcining. The ratio of the surface area after heat treatment compared to the surface area before heat treatment is preferably greater than about 50%, more preferably greater than about 80%. Preferably the change in surface area after heating is at most about 10% and more preferably at most about 5%.

DETAILED DESCRIPTION OF PREFERRED EMBODIMENTS

In one aspect, the present application discloses dental pastes, and methods of making and using dental pastes, that include two fillers dispersed in a hardenable resin. A first filler includes porous, non-pyrogenic silica having a silane treated surface and being substantially free of heavy metal. A second filler includes non-aggregated primary silica particles having a silane treated surface and having an average particle size of at most about 200 nanometers. The dental paste includes at least about 55% by weight based on the total weight of the paste, and preferably at least about 60% by weight based on the total weight of the paste, of the combined first and second fillers. Preferably, the dental pastes have excellent properties for dental operations and can be hardened to fabricate dental articles (e.g., dental mill blanks, dental prostheses, orthodontic devices, artificial crowns, anterior fillings, posterior fillings, and cavity liners) having useful properties.

The use of a combination of different average particle size fillers in dental materials is known in the art. However, such combinations generally result in dental materials that are lacking in one or more desirable properties. For example, some combinations of different average particle size fillers cannot be loaded into a hardenable resin at high enough levels to provide dental pastes that have desirable properties, such as mechanical strength upon curing. Other combinations of different average particle size fillers may provide adequate mechanical strength upon curing, but lack other desirable properties, such as aesthetic qualities upon curing.

In contrast to such dental pastes known in the art, dental pastes disclosed in the present application provide a useful balance of desirable properties. For example, the presently disclosed dental pastes preferably provide, upon hardening, one or more properties including, for example, a contrast ratio of at most about 50, a MacBeth value of at most about 0.4, a volumetric shrinkage of at most about 4%, a diametral tensile strength of at least about 15 MPa, a compressive strength of at least about 35 MPa, and a loss in polish of at most about 30% after 500 brushes in a polish retention test. Preferably dental pastes of the present invention exhibit low visual opacity without the need to match refractive indices of the components. These are properties desired by those of skill in the art for dental pastes and the dental articles that result upon hardening.

In another aspect, the present application discloses dental pastes that include a hardenable resin, and a filler dispersed in the hardenable resin, the filler including porous, non-pyrogenic silica including aggregates of primary silica particles having an average particle size of about 20 nanometers to about 120 nanometers. The filler has a bulk density of at least about 0.4 $g/cm^3$ and a surface area of at most about 150 $m^2/g$. The average size of the aggregated silica in the filler is about 1 micrometer to about 20 micrometers, and the silica is substantially free of heavy metals. Preferably the filler can be dispersed in the hardenable resin to form the dental paste, wherein the paste includes at least about 45% by weight, more preferably at least about 55% by weight, even more preferably at least about 65% by weight, and most preferably at least about 70% by weight of the filler. Preferably the filler includes a silane treated surface.

Fillers Including Porous, Non-Pyrogenic Silica

Fillers including porous, non-pyrogenic silica include amorphous silicas other than fumed or pyrogenic silica. Porous, non-pyrogenic silicas typically include aggregated silica (e.g., aggregates of primary silica particles). Porous, non-pyrogenic silica includes, for example, precipitated silica, silica gel, and silica clusters as described herein. Preferably, the porous, non-pyrogenic silica includes silica gel and/or silica clusters as described herein.

Preferably, the porous, non-pyrogenic silica includes aggregates, and more preferably loosely bound aggregates, of primary silica particles having an average particle size of about 5 nanometers to about 120 nanometers. For some applications, it is preferred that the primary silica particles have an average particle size of at least about 20 nanometers, more preferably at least about 50 nanometers, and most preferably at least about 70 nanometers. For some applications, it is preferred that the primary silica particles have an average particle size of at most about 100 nanometers. Preferably the aggregates are silica clusters having an average size of at least about 1 micrometer. Preferably, the aggregates are silica clusters having an average size of at most about 20 micrometers, and more preferably at most about 10 micrometers. The porous, non-pyrogenic silica is substantially free of heavy metals. Fillers comprising porous, non-pyrogenic silica preferably include at least about 50% by weight, more preferably at least about 80% by weight, and most preferably at least about 90% by weight of aggregated silica.

The porous, non-pyrogenic silica disclosed in the present application preferably includes substantially spherical aggregates of primary silica particles. Preferably the aggregated silica has an average aspect ratio of at most about 4:1, preferably at most about 3:1, more preferably at most about 2:1, and even more preferably at most about 1.5:1.

The porous, non-pyrogenic silica disclosed in the present application preferably has a silane treated surface. The silica can be surface treated before it is added to the resin. The term "surface treatment" is synonymous with surface modifying. The surface treatment for the fillers is discussed below in detail.

The porous, non-pyrogenic silica is preferably treated with a resin-compatibilizing surface treatment agent. Particularly preferred surface treatment agents include silane treatment agents capable of polymerizing with a resin. Preferred silane treatment agents include gamma-methacryloxylpropyltrimethoxysilane, available under the trade designation A174 from Witco OSi Specialties (Danbury, Conn.), gamma-glycidoxypropyltrimethoxysilane, available under the trade designation G6720 from United Chemical Technologies (Bristol, Pa.), a methacryloxyalkyltrimethoxysilane available under the trade designation WACKER SILANE GF 31 from Wacker Silicones (Munich, Germany), and styrylethyltrimethyloxysilane, available from Gelest Inc. (Tullytown, Pa.).

Alternatively a combination of surface treatment agents can be used. Optionally, at least one of the agents has a functional group co-polymerizable with the hardenable resin. For example, the polymerizing group can be ethylenically unsaturated or a cyclic function subject to ring opening polymerization. An ethylenically unsaturated polymerizing group can be, e.g., acrylates, methacrylates or vinyl groups. A cyclic function subject to ring opening polymerization generally contains a heteroatom such as oxygen, sulfur or nitrogen, and preferably is a 3-membered ring containing oxygen such as an epoxide. Other surface modifying agents that do not generally react with hardenable resins can be included to enhance dispersibility or rheological properties. Useful surface modifiying agents include, for example, alkyl polyethers, alkyl-functional silanes, hydroxyalkyl-functional silanes, hydroxyaryl-functional silanes, and aminoalkyl-functional silanes.

The porous, non-pyrogenic silica disclosed in the present application preferably has a bulk density of at least about 0.4 g/cm$^3$, which is a much higher density than found for amorphous silica fillers commonly used in dental pastes. For example, fumed silica typically has a bulk density of 0.03 g/cm$^3$ to 0.12 g/cm$^3$ and precipitated silica typically has a bulk density of 0.03 g/cm$^3$ to 0.3 g/cm$^3$. See Kirk-Othmer Concise Encyclopedia of Chemical Technology, John Wiley & Sons, p. 1054 (New York 1985). While not wishing to be bound by theory, it is believed that the high observed values for bulk density are due to factors including, for example, the ability of the silica clusters to closely pack together and the aggregate morphology, which is related to the porosity.

The porous, non-pyrogenic silica disclosed in the present application preferably has a surface area of at most about 700 m$^2$/g, more preferably at most about 500 m$^2$/g, even more preferably at most about 200 m$^2$/g, even more preferably at most about 150 m$^2$/g, even more preferably at most about 100 m$^2$/g, and most preferably at most about 75 m$^2$/g.

Preparation of Fillers Including Porous, Non-Pyrogenic Silica

A filler in a dry powder form that includes porous, non-pyrogenic silica may be prepared, for example, by the following general method. A volatile liquid silica sol that is substantially free of heavy metals may be dried to give loosely bound aggregates of primary silica particles. Optionally, the size of aggregates may be reduced by, for example, a milling procedure. The aggregated silica may then be redispersed in a volatile liquid and surface treated with a silane to form a volatile liquid dispersion of porous, non-pyrogenic silica having a silane treated surface. The dispersion may then be dried to provide the dry powder.

Preferred silica sols for preparing the porous, non-pyrogenic silica are, for example, commercially available under the trade designation NALCO COLLOIDAL SILICAS from Nalco Chemical Co. (Naperville, Ill.). For example, preferred porous, non-pyrogeinc silica can be prepared using Nalco products 1040, 1042, 1050, 1060, 2327 and 2329. In a preferred embodiment, where the hardenable resin includes a cationic initiation system, the starting silica is preferably an ion exchanged or acidic, non-sodium stabilized silica sol (e.g., Nalco 1042, Nalco 2326, and Nalco 2327). In another preferred embodiment, the starting silica sol is sodium stabilized (e.g., Nalco 2329).

Preferably, the silica sol includes primary particles having an average particle size of about 5 nanometers to about 120 nanometers. For some applications, it is preferred that the primary silica particles have an average particle size of at least about 20 nanometers, more preferably at least about 50 nanometers, and most preferably at least about 70 nanometers. For some applications, it is preferred that the primary silica particles have an average particle size of at most about 100 nanometers.

The silica sol may be dried by any convenient method to form the aggregated silica. Suitable drying methods include, for example, spray drying. The aggregated silica may then be surface treated, or optionally, prior to surface treatment, the average aggregate size may first be reduced by a grinding or milling procedure. Convenient milling procedures include, for example, ball milling and jet milling. If the average aggregate size is reduced, it is preferably reduced to an average aggregate size of about 1 micrometer to about 10 micrometers.

The dry aggregated silica may be redispersed in a volatile liquid for surface treatment with a silane as described above to provide a volatile liquid dispersion of porous, non-pyrogenic silica having a silane treated surface. The volatile liquid dispersion of porous, non-pyrogenic silica having a silane treated surface may be dried by any convenient method to provide the filler in a dry powder form. Suitable drying methods include, for example, spray drying and gap drying (e.g., according to the procedures described in U.S. Pat. No. 5,980,697 (Kolb et al.) and U.S. Pat. No. 5,694,701 (Huelsman, et al.)).

Optionally, the porous, non-pyrogenic silica may be calcined, preferably before the surface treatment step. If the silica is calcined, preferably the temperature is at most about 650° C., more preferably at most about 600° C., and most preferably at most about 550° C. If the silica is calcined, preferably it is calcined for at most about 12 hours, more preferably at most about 6 hours, and most preferably at most about 4 hours.

Fillers Including Non-Aggregated Silica Particles

For some embodiments of the present invention, the dental pastes include an additional filler dispersed in the hardenable resin. The additional filler includes non-aggregated primary silica particles having a silane treated surface and preferably having an average particle size of at most about 200 nanometers, more preferably at most about 150 nanometers, and most preferably at most about 120 nanometers. Preferably the non-aggregated primary silica particles have an average particle size of at least about 20 nanometers, more preferably at least about 50 nanometers, and most preferably at least about 70 nanometers. These measurements are preferably based on a TEM (transmission electron microscopy) method, whereby a population of particles is analyzed to obtain an average particle size. A preferred method for measuring the particle size is set out below in the Test Methods section. The average surface area of the non-aggregated silica particles is preferably at least about 15 $m^2/g$ and more preferably at least about 30 $m^2/g$. Suitable fillers including non-aggregated silica particles and methods of preparing the fillers are disclosed in, for example, International Publication No. WO 01/30307 (Craig et al.).

The non-aggregated silica particles used in the dental pastes disclosed in the present application are preferably substantially spherical and substantially non-porous. Although the silica is preferably essentially pure, it may contain small amounts of stabilizing ions such as ammonium and alkaline metal ions.

Preferred silica sols for preparing the non-aggregated silica particles are, for example, commercially available under the trade designation NALCO COLLOIDAL SILICAS from Nalco Chemical Co. (Naperville, Ill.). For example, preferred silica particles can be obtained from using Nalco products 1040, 1042, 1050, 1060, 2327 and 2329. In a preferred embodiment where the hardenable resin includes a cationic initiation system, the starting silica is preferably an acidic, non-sodium stabilized silica sol (e.g., Nalco 1042). In another preferred embodiment, the starting silica sol is Nalco 2329.

The non-aggregated silica particles can be surface treated. Surface-treating the non-aggregated silica particles before loading into the dental paste can provide a stable dispersion in the resin. "Stable," as used herein, means a dental material in which the particles do not agglomerate after standing for a period of time, such as about 24 hours, under standard ambient conditions (e.g., room temperature (about 20–22° C.), atmospheric pressure, and no extreme electromagnetic forces). Preferably, the surface-treatment stabilizes the non-aggregated silica particles so that the particles will be well dispersed in the hardenable resin and results in a substantially homogeneous composition. Furthermore, it is preferred that the silica be modified over at least a portion of its surface with a surface treatment agent so that the stabilized particles can copolymerize or otherwise react with the hardenable resin during curing.

The non-aggregated silica particles disclosed in the present application are preferably treated with a resin-compatibilizing surface treatment agent. Particularly preferred surface treatment or surface modifying agents include silane treatment agents capable of polymerizing with a resin. Preferred silane treatment agents include γ-methacryloxylpropyltrimethoxysilane available under the trade designation A-174 from Witco OSi Specialties (Danbury, Conn.) and γ-glycidoxypropyltrimethoxysilane available under the trade designation G6720 from United Chemical Technologies (Bristol, Pa.).

Alternatively a combination of surface modifying agents can be useful. Optionally, at least one of the agents has a functional group co-polymerizable with a hardenable resin. For example, the polymerizing group can be ethylenically unsaturated or a cyclic functionality subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur, or nitrogen, and preferably is a 3-membered ring containing oxygen (e.g., an epoxide). Other surface modifying agents that do not generally react with hardenable resins can be included to enhance dispersibility or rheological properties. Useful surface modifiying agents include, for example, alkyl polyethers, alkyl-functional silanes, hydroxyalkyl-functional silanes, hydroxyaryl-functional silanes, and aminoalkyl-functional silanes.

The non-aggregated silica particles are preferably surface treated in a volatile liquid dispersion. After the surface treatment, the silica particles can be combined with an appropriate hardenable resin composition to form a dental paste. For example, the volatile liquid dispersion of the surface treated silica particles can be dried to provide a filler in a dry powder form including non-aggregated silica particles having a silane treated surface.

Hardenable Resins

Dental pastes of the present invention include a hardenable resin. These resins preferably are generally thermosetting materials capable of being hardened to form a polymer network including, for example, acrylate-functional materials, methacrylate-functional materials, epoxy-functional materials, vinyl-functional materials, and mixtures thereof. Preferably, the hardenable resin is made from one or more matrix-forming oligomer, monomer, polymer, or blend thereof.

In a preferred embodiment where the dental paste disclosed in the present application is a dental composite, polymerizable materials suitable for use include hardenable organic materials having sufficient strength, hydrolytic stability, and non-toxicity to render them suitable for use in the oral environment. Examples of such materials include acrylates, methacrylates, urethanes, carbamoylisocyanurates, epoxies (e.g., those shown in U.S. Pat. No. 3,066,112 (Bowen); U.S. Pat. No. 3,539,533 (Lee II et al.); U.S. Pat. No. 3,629,187 (Waller); U.S. Pat. No. 3,709,866 (Waller); U.S. Pat. No. 3,751,399 (Lee et al.); U.S. Pat. No. 3,766,132 (Lee et al.); U.S. Pat. No. 3,860,556 (Taylor); U.S. Pat. No. 4,002,669 (Gross et al.); U.S. Pat. No. 4,115,346 (Gross et al.); U.S. Pat. No. 4,259,117 (Yamauchi et al.); U.S. Pat. No. 4,292,029 (Craig et al.); U.S. Pat. No. 4,308,190 (Walkowiak et al.); U.S. Pat. No. 4,327,014 (Kawahara et al.); U.S. Pat. No. 4,379,695 (Orlowski et al.); U.S. Pat. No. 4,387,240 (Berg); U.S. Pat. No. 4,404,150 (Tsunekawa et al.)); and mixtures and derivatives thereof.

One class of preferred hardenable materials includes materials having free radically active functional groups. Examples of such materials include monomers having one or more ethylenically unsaturated group, oligomers having one or more ethylenically unsaturated group, polymers having one or more ethylenically unsaturated group, and combinations thereof. Alternatively, the hardenable resin can be selected from materials that include cationically active functional groups. In another alternative, a mixture of hardenable resins that include both cationically curable and free radically curable materials may be used for the dental materials of the invention. In another alternative, the hardenable resin can be a material from the class of materials that includes both cationically active and free radically active functional groups in the same molecule.

Free Radically Active Materials. In the class of hardenable resins having free radically active functional groups, suitable materials for use in the invention contain at least one ethylenically unsaturated bond, and are capable of undergoing addition polymerization. Such free radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200-500, copolymerizable mixtures of acrylated monomers such as those in U.S. Pat. No. 4,652,274 (Boettcher et al.), and acrylated oligomers such as those of U.S. Pat. No. 4,642,126 (Zador); and vinyl compounds such as styrene, diallyl phthalate, divinyl succinate, divinyl adipate and divinylphthalate. Mixtures of two or more of these free radically polymerizable materials can be used if desired.

Free Radical Initiation Systems. For free radical polymerization (e.g., hardening), an initiation system can be selected from systems that initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 800 nanometers.

A variety of visible or near-IR photoinitiator systems may be used for photopolymerization of free-radically polymerizable materials. For example, a photoinitiation system can be selected from systems which initiate polymerization via a two component system of an amine and an α-diketone as described in U.S. Pat. No. 4,071,424 (Dart et al.). Alternatively, the material can be combined with a three component photoinitiator system such as described in U.S. Pat. No. 5,545,676 (Palazzotto et al.). The three component system includes an iodonium salt (e.g., a diaryliodonium salt), a sensitizer, and a donor. Each photoinitiator component is described in U.S. Pat. No. 5,545,676, column 2, line 27, to column 4, line 45.

Other useful free-radical initiators include the class of acylphosphine oxides, as described in European Pat. Application Publ. No. 173,567 (Ying) and U.S. Pat. No. 4,737,593 (Ellrich et al.) and U.S. Pat. No. 6,020,528 (Leppard et al.). Tertiary amine reducing agents may be used in combination with an acylphosphine oxide.

Another free-radical initiator system that can alternatively be used in the dental materials of the invention includes the class of ionic dye-counterion complex initiators including a borate anion and a complementary cationic dye. Borate salt photoinitiators are described, for example, in U.S. Pat. No. 4,772,530 (Gottschalk et al.), U.S. Pat. No. 4,954,414 (Adair et al.), U.S. Pat. No. 4,874,450 (Gottschalk), U.S. Pat. No. 5,055,372 (Shanklin et al.), and U.S. Pat. No. 5,057,393 (Shanklin et al.).

Yet another alternative class of initiators capable of initiating polymerization of free radically active functional groups in the hardenable resin includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least about 40° C. and at most about 150° C. under normal conditions or at elevated pressure. This procedure is preferred for initiating polymerization of materials occurring outside of the oral environment.

Yet another alternative class of initiators capable of initiating polymerization of free radically active functional groups in the hardenable resin are those that include free radical-generating thermal initiators. Examples include peroxides (e.g., benzoyl peroxide and lauryl peroxide) and azo compounds (e.g., 2,2-azobis-isobutyronitrile (AIBN)).

Cationically Active Materials. An alternative class of hardenable resins useful in dental pastes disclosed in the present application includes materials having cationically active functional groups. Materials having cationically active functional groups include cationically polymerizable epoxies, vinyl ethers, oxetanes, spiro-orthocarbonates, spiro-orthoesters, and the like. Preferred materials having cationically active functional groups are epoxy-functional materials including, for example, those disclosed in U.S. Pat. No. 6,025,406 (Oxman et al.) (e.g., column 2, line 36 to column 4, line 52) and in the documents cited therein.

Optionally, monohydroxy- and polyhydroxy-alcohols may be added to the hardenable resin, as chain-extenders for a hardenable resin having cationically active functional groups, which are preferably epoxy-functional materials. The hydroxyl-containing material used in the present invention can be any organic material having hydroxyl functionality of at least about 1, and preferably at least about 2. Useful hydroxyl-containing materials are described, for example, in U.S. Pat. No. 5,856,373 (Kaisaki et al.).

For hardening resins including cationically active functional groups, an initiation system can be selected from systems that initiate polymerization via radiation, heat, or redox/auto-cure chemical reactions. For example, epoxy polymerization may be accomplished by the use of thermal curing agents including, for example, anhydrides and amines. A particularly useful example of an anhydride curing agent is cis-1,2-cyclohexanedicarboxylic anhydride.

Alternatively, initiation systems for resins including cationically active functional groups are those that are photoactivated. The broad class of cationic photoactive groups recognized in the catalyst and photoinitiator industries may be used in the practice of the present invention. Photoactive cationic nuclei, photoactive cationic moieties, and photoactive cationic organic compounds are art recognized classes of materials as exemplified by, for example, U.S. Pat. No. 4,250, 311 (Crivello); U.S. Pat. No. 3,708,296 (Schlesinger); U.S.

Pat. No. 4,069,055 (Crivello); U.S. Pat. No. 4,216,288 (Crivello); U.S. Pat. No. 5,084,586 (Farooq); U.S. Pat. No. 5,124,417 (Farooq); U.S. Pat. No. 4,985,340 (Palazzotto et al.), U.S. Pat. No. 5,089,536 (Palazzotto), and U.S. Pat. No. 5,856,373 (Kaisaki et al.).

The cationically-curable materials can be combined with a three component or ternary photoinitiator system, as described above, for example, using an iodonium salt, a sensitizer, and an electron donor. For hardening cationically curable materials, examples of useful aromatic iodonium complex salts are disclosed in U.S. Pat. No. 6,025,406 (Oxman et al.) (e.g., column 5, line 46, to column 6, line 9). Examples of useful sensitizers and electron donors can also be found in U.S. Pat. No. 6,025,406 (e.g., column 6, line 43, to column 9, line 43).

An alternative photoinitiator system for cationic polymerizations includes the use of organometallic complex cations essentially free of metal hydride or metal alkyl functionality selected from those described in U.S. Pat. No. 4,985,340 (Palazzotto et al.).

Cationically Active/Free Radically Active Materials. Alternatively, the hardenable resins may have both cationically active and free radically active functional groups contained in a single molecule. Such molecules may be obtained, for example, by reacting a di- or poly-epoxide with one or more equivalents of an ethylenically unsaturated carboxylic acid. An example of such a material is the reaction product of a material, which is available under the trade designation UVR-6105 from Union Carbide, with one equivalent of methacrylic acid. Commercially available materials having epoxy and free-radically active functionalities include materials available under the trade designation CYCLOMER (e.g., CYCLOMER M-100, M-101, or A-200) from Daicel Chemical, Japan, and the material available under the trade designation EBECRYL-3605 from Radcure Specialties.

Photoinitiator compounds are preferably provided in dental pastes disclosed in the present application in an amount effective to initiate or enhance the rate of cure or hardening of the resin system. Useful photopolymerizable compositions are prepared by simply admixing, under safe light conditions, the components as described above. Suitable inert solvents may be used, if desired, when preparing this mixture. Any solvent that does not react appreciably with the components of the inventive compositions may be used. Examples of suitable solvents include, for example, acetone, dichloromethane, and acetonitrile. A liquid material to be polymerized may be used as a solvent for another liquid or solid material to be polymerized. Solventless compositions can be prepared, for example, by simply dissolving an aromatic iodonium complex salt and sensitizer in an epoxy-functional material/polyol mixture with or without the use of mild heating to facilitate dissolution.

Other Additives

The inventive dental pastes and articles may optionally include additives suitable for use in the oral environment including, for example, colorants, flavorants, anti-microbials, fragrances, stabilizers, viscosity modifiers, and fluoride releasing materials. For example, a fluoride releasing glass may be added to dental pastes of the present invention to provide the benefit of long-term release of fluoride in use, for example in the oral cavity. Fluoroaluminosilicate glasses are particularly preferred. Particularly preferred fluoroaluminosilicate glasses are those that have been silanol treated as described, for example, in U.S. Pat. No. 5,332,429 (Mitra et al.). Other suitable additives include, for example, agents that impart fluorescence and/or opalescence.

Optionally, dental pastes, dental articles, and compositions of the present invention may also include fumed silica. Suitable fumed silicas include for example, products available under the trade designations AEROSIL OX-50, AEROSIL-130, AEROSIL-150, and AEROSIL-200 available from DeGussa AG, (Hanau, Germany) and CAB-O-SIL M5 available from Cabot Corp (Tuscola, Ill.).

Incorporation of Fillers into Resins

Fillers disclosed in the present application may be incorporated into and dispersed in a hardenable resin by any suitable means to form a dental paste.

Porous, non-pyrogenic silica having a silane treated surface may conveniently be added to the hardenable resin as a powder. Alternatively, the silica may be combined with another filler and/or optional additives to provide a material that is then added to the hardenable resin as a powder. Alternatively, the silica may be combined with liquid additives and added to the hardenable resin as a dispersion.

Additional filler including non-aggregated primary silica particles having a silane treated surface and having an average particle size of at most about 200 nanometers may be added to the hardenable resin by a variety of methods. For example, a solvent exchange procedure may be used to add a surface modified sol to the resin, followed by removal of water and co-solvent (if used) by evaporation, thus leaving the particles dispersed in the hardenable resin. The evaporation step can be accomplished, for example, by distillation, rotary evaporation, or oven drying. Another method for incorporating non-aggregated primary silica particles into the resin involves drying the surface modified particles into a powder. The powder can then be dispersed in the resin. In still another method, the non-aggregated primary silica particles can be isolated by filtration to obtain solids that can be dried into a powder. This method is preferred when the particles of the surface modified aqueous sol have agglomerated due to the incompatibility of the surface treatment with the aqueous medium. The resin and the dry, filtered particles are then combined.

The fillers disclosed in the present application may be dispersed in the hardenable resin by any convenient method known in the art.

Dental Pastes

Fillers disclosed in the present application can be incorporated into a hardenable resin to provide useful dental pastes as described above. Dental pastes of the present invention can be chemically curable, heat curable or light curable compositions. Light curable materials should have an appropriate initiator system. Chemically curable materials can be auto-cure (e.g. via redox initiators). Alternatively, the materials of the invention can be hardened by a combination of auto- and light-cure.

Dental pastes disclosed in the present application include fillers dispersed in a hardenable resin, wherein the fillers include porous, non-pyrogenic silica having a silane treated surface and being substantially free of heavy metal. Preferably the dental paste includes at least about 10% by weight porous, non-pyrogenic silica, more preferably at least about 20% by weight porous, non-pyrogenic silica, and most preferably at least about 30% by weight porous, non-pyrogenic silica. Preferably the dental paste includes at most about 70% by weight porous, non-pyrogenic silica, more preferably at most about 50% by weight porous, non-pyrogenic silica, and most preferably at most about 40% by weight porous, non-pyrogenic silica.

For some embodiments of the present invention, the dental paste may also include an additional filler dispersed in the hardenable resin. The additional filler includes non-aggregated primary silica particles having a silane treated surface and having an average particle size of at most about 200 nanometers. Such a dental paste preferably includes at least about 20% by weight non-aggregated primary silica particles, more preferably at least about 30% by weight non-aggregated primary silica particles, and most preferably at least about 40% by weight non-aggregated primary silica particles. Such a dental paste preferably includes at most about 70% by weight non-aggregated primary silica particles, more preferably at most about 60% by weight non-aggregated primary silica particles, and most preferably at most about 50% by weight non-aggregated primary silica particles.

When a dental paste includes fillers including porous, non-pyrogenic silica and fillers including non-aggregated silica particles, the fillers are preferably in a weight ratio of at least about 1:4, more preferably at least about 2:4, and most preferably at least about 3:4, respectively. When a dental pastes includes fillers including porous, non-pyrogenic silica and fillers including non-aggregated silica particles, the fillers are preferably in a weight ratio of most about 4:1, more preferably at most about 4:2, and most preferably at most about 4:3.

The dental pastes disclosed in the present application can be used, for example, as dental adhesives, artificial crowns, anterior or posterior fillings, casting materials, cavity liners, cements, coating compositions, mill blanks, orthodontic devices, restoratives, prostheses, and sealants. In a preferred aspect, the dental paste is a dental restorative. The restoratives of the invention can be placed directly in the mouth and cured (hardened) in situ, or alternatively, may be fabricated into a prosthesis outside the mouth and subsequently adhered in place inside the mouth.

It has been found that dental pastes of the invention, although filled at relatively high filler levels still possess useful rheological properties (e.g., soft, non-sticky). These properties as well as strength are believed to be enhanced by the use of surface-modifying agents to treat the surface of the particles. Surface treatment (surface-modification) enhances the dispersibility of the porous silica and silica particles and their ability to bind into the matrix.

Practitioners generally desire reasonable handling properties in a dental paste, as it often translates to time savings. For example, in dental restorative work, it is desirable that dental pastes do not slump (e.g., flow or change in shape), because after a practitioner places the paste in the mouth and manipulates the paste by contouring and feathering, the practitioner generally wants the imparted shape to remain unchanged until the paste is hardened. Pastes used for restorative work, having a sufficiently high yield stress generally will not slump; that is, they will not flow under the stress of gravity. The yield stress of a paste is the minimum stress required to cause the paste to flow, and is described in "Rheology Principles, Measurements, and Applications" by C. W. Macosko, VCH Publishers, Inc., New York, 1994, p. 92. If the stress due to gravity is below the yield stress of the paste, then the paste will not flow. The stress due to gravity, however, will depend on the mass of dental paste being placed as well as the shape.

"Contouring" refers to the process of shaping a paste (using dental instruments) so that it resembles the natural dental anatomy. For easy contouring, pastes should have a sufficiently high viscosity that they maintain their shape after manipulation with a dental instrument, and yet the viscosity should not be so high that it is difficult to shape the paste. "Feathering" refers to the process of reducing the dental paste to a thin film in order to blend the paste into the natural dentition. This is done with a dental instrument at the margin of the manipulated paste and the natural dentition. It is also desirable that the dental paste not stick to placement instruments, to minimize further alteration of the shape or surface topography.

In a preferred embodiment where the dental paste of the invention is a restorative, the dental paste preferably has little to no slump, yet easily adapts to, for example, a cavity preparation, and is easily contoured and feathered. Preferably, the dental pastes of the invention do not stick to placement instruments, and are advantageously, overall, fast and easy to use in dental procedures such as, for example, restoring tooth structure.

Preferably, the present invention provides dental pastes that are capable of being hardened to provide a balance of desirable properties as detailed below (e.g., a low opacity, a low volumetric shrinkage value, a high diametral tensile strength, a high compressive strength, and a high retention of gloss upon polishing) while retaining excellent handling properties (e.g., soft, non-sticky). Preferably, the dental paste is non-sticky when handled using well known procedures by one of skill in the art. Stickiness can also be measured, for example, with a texture analyzer as described in the Examples, with lower values for the ratio of String Work Done/Hardness (SWD/Hardness) indicating a less sticky paste. Preferably the dental paste has a value for SWD/Hardness of at most about 0.5, more preferably at most about 0.4, and most preferably at most about 0.2.

Hardened Dental Compositions

It has been found that loading a dental paste with fillers disclosed in the present application imparts a desirable combination of strength and translucency properties. Dental pastes including porous, non-pyrogenic silica fillers and non-aggregated silica particle fillers as disclosed in the present application have especially desirable handling (rheological) properties in an unhardened state and high strength in a hardened state coupled with desirable aesthetic characteristics.

Strength can be characterized by mechanical measurements such as compressive strength (CS) and diametral tensile strength (DTS). High compressive strength in a dental material is advantageous due to the forces exerted by mastication on dental repairs, replacements and restorations. Diametral tensile strength indicates the dental material's ability to withstand compression forces that introduce a tensile stress in the material. Tests for each strength measurement are set out below in the Examples.

The dental pastes disclosed in the present application, when hardened, preferably have a compressive strength of at least about 35 MPa; more preferably, the materials have a compressive strength of at least about 200 MPa; and most preferably, the materials have a compressive strength of at least about 350 MPa. Hardened dental pastes of the invention preferably have a diametral tensile strength of at least about 15 MPa; more preferably at least about 40 MPa; and most preferably at least about 60 MPa.

Hardened dental pastes disclosed in the present application preferably exhibit low shrinkage upon hardening. Shrinkage can be measured by, for example, the following procedure that measures the volumetric shrinkage of a sample after polymerization. A 120 mg portion of each sample is weighed out. The procedures described in "Determination of Polymerization Shrinkage Kinetics in Visible-Light-Cured Materials: Methods Development" (Dental Materials, October 1991, pgs 281–286) are used to prepare and test the samples with the following exceptions. A 1 mm thick brass ring is used. Output signals are acquired through an analog-to-digital converter in a microcomputer using LabView (National Instruments, Bridgeview Tex.) automation software. Each sample is cured for 60 seconds with a Visilux 2™ (3M, St. Paul, Minn.) with data collection starting at the time of cure and continuing during 5 minutes of post-cure. Three replicates are performed for each sample. Preferably, dental pastes of the present invention, upon curing, exhibit a volumetric shrinkage of at most about 4%, more preferably at most about 3.5%, and most preferably at most about 3%.

Hardened dental pastes disclosed in the present application preferably exhibit desirable aesthetic qualities including high translucency, high gloss, and high retention of polish after exposure to repetitive abrasion.

Aesthetic quality of a dental material, although a somewhat subjective characteristic (yet well-understood in the dental industry), can be preferably quantified in one aspect, by measuring MacBeth values, in which lower MacBeth values indicate a lower visual opacity. Visual opacity is indicative of dental material's level of translucency. Low visual opacity is desired so that the hardened dental material will have a life-like luster. The dental materials disclosed in the present application preferably have a MacBeth value of at most about 0.4, more preferably at most about 0.3, and most preferably at most about 0.2.

Alternatively, the translucency of a hardened paste may be determined by a contrast ratio measurement, in which a lower contrast ratio value indicates a lower visual opacity. The dental materials disclosed in the present application preferably have a contrast ratio of at most about 50, more preferably at most about 40, and most preferably at most about 30.

High translucency of a hardened dental paste contributes to the aesthetic character and quality of the material. Polishability of a hardened dental paste also contributes to the aesthetic character and quality of the material. The ability of a dental material to have a glossy finish and life-like luster upon polishing is highly desirable. An even greater benefit is the ability of a hardened paste to retain its luster even after repetitive abrasive contact, such as tooth brushing. It has been surprisingly found that materials disclosed in the present application (e.g., hardenable resin including both porous, non-pyrogenic silica and silica particles) preferably have high polishability and are able to retain the polish and luster after repetitive tooth brushing.

To evaluate a hardened, polished dental material's ability to retain its polish, a polish retention test can be performed as described herein in the Examples. Briefly, the polish retention can be determined by measuring specularly reflected light from the sample surface after polishing and after toothbrushing. For example, a micro-tri-gloss instrument (BYK Gardner, Columbia, Md.) can be used to collect photoelectric measurements of specularly reflected light from the sample surface after polishing and after toothbrushing using a procedure as described in the Examples. After subjecting the dental materials of the invention to the polish retention test with 500 toothbrushing cycles, the dental materials preferably have a loss of gloss of at most about 30%, more preferably at most about 20%, and most preferably at most about 10%.

Dental Articles

The pastes of the present invention may be hardened to form, for example, dental articles. In a preferred method of using dental pastes including a hardenable resin and fillers as disclosed in the present application, the paste may be placed near or on a tooth surface, followed by a manipulation by the practitioner or laboratory to change the topography of the paste, then the resin may be hardened. These steps can be followed sequentially or in a different order. For example, in a preferred embodiment where the dental material is a mill blank or a prosthesis, the hardening step is generally completed prior to changing the topography of the paste. Changing the topography of the paste can be accomplished in various ways including, for example, carving or manual manipulation using hand held instruments, or by machine or computer aided apparatus (e.g., a CAD/CAM milling machine) in the case of prostheses and mill blanks. Optionally, a finishing step can be performed to polish, finish, or apply a coating on the dental material.

The present invention is illustrated by the following examples. It is to be understood that the particular examples, materials, amounts, and procedures are to be interpreted broadly in accordance with the scope and spirit of the invention as set forth herein.

EXAMPLES

The following examples are given to illustrate, but not limit, the scope of this invention. Unless otherwise indicated, all parts and percentages are by weight and all molecular weights are weight average molecular weight.

TABLE 1

Abbreviations, Descriptions, And Sources Of Materials

| Abbreviation | Description | Source |
| --- | --- | --- |
| Bis-GMA | 2,2-Bis[4-(2-hydroxy-3-methacryloyloxy-propoxy)phenyl]propane | CAS No. 1565-94-2 |
| UDMA | Diurethane Dimethacrylate (CAS No. 41137-60-4), commercially available as Rohamere 6661-0 | Rohm Tech, Inc., Malden, MA |
| Bis-EMA6 | Ethoxylated (6 mole ethylene oxide) Bisphenol A Dimethacrylate (CAS No. 41637-38-1) | Sartomer CD541, Sartomer Co., Exton, PA |
| TEGDMA | Triethyleneglycol Dimethacrylate | Sartomer Co. |
| CPQ | Camphorquinone | Sigma-Aldrich, St. Louis, MO |
| DPIHFP | Diphenyl Iodonium Hexafluorophosphate | Johnson Matthey, Alpha Aesar Division, Ward Hill, NJ |
| EDMAB | Ethyl 4-Dimethylaminobenzoate | Sigma-Aldrich |
| BHT | 2,6-Di-tert-butyl-4-methylphenol | Sigma-Aldrich |
| NORBLOC 7966 | 2-(2'-Hydroxy-5'-methacryloxyethylphenyl)-H-benzotriazole (CAS No. 96478-09-0) | Janssen Pharmaceuticals, Titusville, PA |
| A174 | γ-Methacryloxypropyltrimethoxysilane | Witco Osi Specialties, Danbury, CT |

TABLE 1-continued

Abbreviations, Descriptions, And Sources Of Materials

| Abbreviation | Description | Source |
|---|---|---|
| Nalco 1042 | Colloidal silica sol (pH about 3.2, nominal particle size about 20 nanometers, solids content about 35%) | Nalco, Naperville, IL |
| Nalco 2329 | Sodium hydroxide stabilized colloidal silica sol (pH about 8–9, nominal particle size about 75 nanometers, solids content about 40%) | Nalco |
| None | Methoxy-2-propanol | Sigma-Aldrich |
| None | Zirconyl Acetate | Magnesium Elektron, Inc., Flemington, NJ |
| MICRO-90 | Surfactant | Cole-Parmer (Vernon Hills, NY) |
| Silica Gel I | White powder having the following properties: 8 micrometer average particle size, 469 m$^2$/g surface area, 0.817 ml/g pore volume, and 6.9 nanometers average pore diameter | AnalytiChem Corporation (Harbor City, CA) |
| Silica Gel II | White powder having the following properties: 5–25 micrometer average particle size, 500 m$^2$/g surface area, 0.75 ml/g pore volume, and 6 nanometers average pore diameter | Sigma-Aldrich |

Test Methods

Average Particle Size Determination (TEM): Samples approximately 80-nm thick were placed on 200-mesh copper grids with carbon stabilized formvar substrates (SPI Supplies, a division of Structure Probe, Inc., West Chester, Pa.). A transmission electron micrograph (TEM) was taken using a JEOL 200CX Instrument (JEOL, Ltd. of Akishima, Japan and sold by JEOL USA, Inc.) at 200 Kv. A population size of about 50–100 particles was measured and an average particle size was determined.

Cluster Size Determination: Cluster size distribution (based on volume percent) was determined using a Coulter LS 230 Particle Size Analyzer (Coulter Corporation, Hialeah, Fla.). The Analyzer was equipped with a Polarization Intensity Differential Scanning (PIDS) software. A 300-mg sample of filler was added into a glass vial with enough MICRO-90 surfactant to wet all the filler. A 30-ml aliquot of Calgon Solution (made by thoroughly mixing 0.20 g sodium fluoride, 4.00 g sodium pyrophosphate, 40.00 g sodium hexametaphosphate, 8.00 g MICRO-90 surfactant, and 3948 ml of DI water) was added and the resulting mixture shaken for 15 minutes and sonicated by a probe sonicator (Model W-225 Sonicator, Heat Systems-Ultrasonics, Farmingdale, N.Y.) for 6 min at an output control knob setting of 9. Particle analysis was conducted using Coulter LS 230 Particle Characterization Software Version 3.01. Testing conditions were 90 seconds for Run Length, 0 seconds for Wait Length, and the test sample was added dropwise into the sample orifice until the PIDS reading was between 45% and 55%. Three sets of data per sample were averaged to obtain the average cluster size.

Handling Properties: Handling properties, e.g., tackiness or stickiness of a paste sample, were measured with a texture analyzer using a Stevens Mechtric QTS Twenty Five (Model number: 7113-25 kg) from Leonard Farnell & Co. Ltd. (Hatfield, Hertfordshire, England). A paste sample was placed in a cylindrical, plastic cup (11-mm inner diameter×6-mm deep), smoothed flat at the top, and placed for 30 minutes on a heating plate set at 28° C. The cup was placed into the sample holder in the heating plate and the test was begun by clicking "Run Test". The probe used was a 4.5-mm stainless steel cylinder (45MMSS), the stop for the boom was set around −8.5, and the computer program was called QTS with settings parameters as follows: Test Number=50, Total Cycles=1, Hold Time=0 seconds, Recovery Time=0 seconds, Trigger Point=5.0 g, Test Speed=70 mm/minute, Target Value=3.000 mm, Target Unit=Distance, and Target Test=Compression. Three tests were run for each paste sample and the average and standard deviation of the three measurements of Hardness (in gram (g) units) and Stringiness Work Done (in gram-second (gs) units) were recorded. The ratio of String Work Done to Hardness (in second (s) units) was then calculated with a lower number indicating a less sticky paste.

Visual Opacity (MacBeth Values and Contrast Ratio): Disc-shaped (1-mm thick×20-mm diameter) paste samples were cured by exposing them to illumination from a VISILUX 2 curing light (3M Co, St. Paul, Minn.) for 60 seconds on each side of the disk at a distance of 6 mm, followed by additional curing for 90 seconds in a DENTACOLOR XS light box (Kulzer, Inc., Germany). Hardened samples were measured for direct light transmission by measuring transmission of light through the thickness of the disk using a MacBeth transmission densitometer Model TD-903 equipped with a visible light filter, available from MacBeth (MacBeth, Newburgh, N.Y.). Lower MacBeth Values indicate lower visual opacity and greater translucency of a material. The reported values are the average of 3 measurements.

Alternatively, the translucency of a hardened sample (prepared as described in the preceding paragraph) could be determined by measuring Contrast Ratio as follows. ASTM-D2805-95 test method was modified to measure the Contrast Ratio (or opacity) of the disks. Y-tristimulus values for the disks were measured on an Ultrascan XE Colorimeter (Hunter Associates Laboratory, Reston, Va.) with a 0.953-cm aperture using separate white and black backgrounds. The D65 Illuminant was used with no filters for all measurements. A 10° angle of view was used. The Contrast Ratio or opacity, C, was calculated as the ratio of the reflectance through a material on a black substrate to the reflectance through an identical material on a white substrate. Reflectance is defined as equal to the Y-tristimulus value. Thus, C=RB/RW, where RB=reflectance through a sample on a black substrate and RW=reflectance through the same sample on a white substrate. Reported Contrast Ratio values are from single measurements with lower values indicative of greater translucency (i.e., transmission of light).

Polish Retention: The polish retention of a hardened sample was measured by the following method. Rectangular-shaped paste samples (20-mm long×9-mm wide×3-mm thick) were cured with a VISILUX 2 unit for 80 seconds followed by additional curing for 90 seconds in a DENTA-COLOR XS light box (Kulzer, Inc., Germany). The samples were mounted with double-sided adhesive tape (Scotch Brand Tape, Core series 2-1300, St. Paul, Minn.) to a holder and were polished according to the following series of steps that were performed sequentially as shown in Table 2. A Buehler ECOMET 4 Polisher with an AUTOMET 2 Polishing Head was used with clockwise rotation.

TABLE 2

Polishing Sequence of Steps

| Step No. | Procedure (Abrasive-Grit) | Lubricant | RPM | Load (Kg) per sample | Time (Seconds) |
|---|---|---|---|---|---|
| 1 | Polish (SiC-320) | Water | 150 | 0.45 | 40 |
| 2 | Rinse | Water | | | |
| 3 | Polish (SiC-600) | Water | 150 | 0.45 | 60 |
| 4 | Rinse | Water | | | |
| 5 | Polish (9-mm diamond paste). | Oil | 130 | 0.45 | 120 |
| 6 | Rinse | Water, soapy water, isopropanol | | | |
| 7 | Polish (3-mm diamond paste). | Oil | 130 | 0.45 | 120 |
| 8 | Rinse | Water, soapy water, isopropanol | | | |
| 9 | Polish (Master Polish Solution) | Water | 120 | 0.34 | 100 |
| 10 | Rinse | Water, soapy water, isopropanol | | | |

A micro-tri-gloss instrument (BYK Gardner, Columbia, Md.) was used to collect photoelectric measurements of specularly reflected light from the sample surface after polishing and after toothbrushing. The procedure described in ASTM D 523-89 (Reapproved 1994) Standard Test Method for Specular Gloss, for measurements made at 60° geometry was followed with the following modification. Initial gloss after polishing ($G_I$) was measured for initial sample. Final gloss after 500 toothbrushing cycles ($G_F$) was measured. A $\Delta G$ value was calculated with the following formula: $\Delta G = (G_F) - (G_I)$. Randomly selected areas on the rectangular sample were measured for initial and final gloss. Each sample was brushed for a total of 500 cycles with an ORAL B 40 medium Straight toothbrush (Oral B Laboratories, Belmont, Calif.) using CREST Regular Flavor (Proctor & Gamble, Cincinnati, Ohio) toothpaste. One operator brushed all of the samples using forces on the order of toothbrushing forces. Each sample was brushed with the same toothbrush. One toothbrushing cycle was a forward and a back stroke.

Compressive Strength (CS) and Diametral Tensile Strength (DTS): ADA ("American Dental Association") specification No. 9 and ADA specification No. 27 respectively of ISO-test procedure 4049 (1988) were followed for all Compressive Strength (CS) and Diametral Tensile Strength (DTS) testing. Specifically, paste samples were packed into 4-mm inside diameter glass tubes, capped with silicone rubber plugs, axially compressed at about 0.28 MPa for 15 minutes, and then light cured for 80 seconds by exposure to two oppositely-disposed VISILUX 2 (3M Co, St. Paul, Minn.) units. Each sample was then irradiated for 90 seconds using a Dentacolor XS unit (Kulzer, Inc., Germany). Cured samples were cut on a diamond saw to form cylindrical plugs 8-mm long for measurement of CS and 2-mm long for measurement of DTS. The plugs were stored in distilled water at 37° C. for 24 hours. CS and DTS values for each composition were measured using an INSTRON (Instron 4505, Instron Corp. Canton, Mass.) with a 10 kN load cell. The DTS results reported are the average of 5 measurements and the CS results are the average of 3 measurements.

Filler Bulk Density: Filler material was poured into a pre-weighed 10-ml glass graduate cylinder to the 10-ml mark and the cylinder was tapped by hand for 20–30 times. If the filler level decreased with tapping, additional filler material was added to the cylinder to again reach the 10-ml mark. The tapping and adding filler steps were repeated for three more times with the final filler addition again reaching exactly to the 10-ml mark. The filled cylinder was weighed and the weight of added filler calculated by difference. The filler bulk density was calculated by dividing the filler weight (grams) by the volume (10 ml).

Starting Materials

Liquid Resin A: Liquid Resin A was made by blending together the components listed in Table 3.

TABLE 3

Components of Liquid Resin A

| Component | Parts by Weight |
|---|---|
| bis-GMA | 24.18 |
| UDMA | 33.85 |
| Bis-EMA6 | 33.85 |
| TEGDMA | 4.84 |
| CPQ | 0.2 |
| DPIHFP | 0.5 |
| EDMAB | 1.0 |
| BHT | 0.1 |
| NORBLOC 7966 | 1.5 |

Filler A (Silane-Treated Nano-Sized Silica Particles): Silane-treated, non-aggregated, nano-sized silica particles in the form of a dry powder were prepared according to the following procedure. Nalco 2329 silica sol (400.82 g) was charged to a one-quart jar. Methoxy-2-propanol (250.28 g) and A174 (6.15 g) were mixed together and added to the silica sol with stirring for about 5 minutes. The jar was sealed and heated to 80° C. for 16 hours. The resulting white dispersion was dried using a gap drying process according to the procedures described in U.S. Pat. No. 5,980,697 (Kolb et al.) and U.S. Pat. No. 5,694,701 (Huelsman, et al.), with a dispersion coating thickness of about 35-mil (0.9-mm) and a residence time of 1.6 minutes (heating platen temperature 143° C. and condensing platen temperature 21° C.) to yield a fine, free-flowing white powder that was designated Filler A. The nominal particle size of Filler A was assumed to be the same as in the starting Nalco silica sol, i.e., about 75 nanometers.

Filler B (Silane-Treated Silica-Zirconia Clusters): Silane-treated, nano-sized silica and zirconia particles loosely aggregated as substantially amorphous clusters were prepared in the form of a dry powder according to the following procedure. A 5.0-kg portion of Nalco 1042 silica sol was adjusted to a pH of 2.5 using dilute nitric acid. The pH-adjusted sol was added slowly to zirconyl acetate (2.95 kg) and the resulting mixture stirred for 1 hour. This mixture was then spray dried using a 91-cm Niro Spray Drier (Niro MOBILE MINOR Spray Drier, Columbia, Md.) at a 325° C. inlet temperature and a 120° C. outlet temperature. The resulting solid was heat-treated (calcined) at 550° C. for 4 hours. The calcined solid was ball-milled for 160 hours to yield a white powder that was determined according to the Cluster Size Determination Test Method described herein to consist of clusters having an average size of 2 micrometers.

A 20-g sample of the white powder was thoroughly mixed with deionized (DI) water (40 g) by stirring for 2 minutes with a magnetic stir bar. The resulting homogeneous mixture was adjusted to a pH of 8.5 with ammonium hydroxide. A174 (1.7 g) was added, the contents thoroughly mixed for 120 minutes using a magnetic stir bar, and the resulting mixture adjusted to a final pH of 8.25. The mixture was then spray dried using a Buchi spray drier (Buchi/Brinkman Mini Spray Dryer, Model 190, Brinkmann Instruments, Inc., Westbury, N.Y.) at 200° C. inlet temperature and 85° C. outlet temperature. The resulting fine, free-flowing white powder was designated Filler B.

Filler C (Silane-Treated Fumed Silica): A silanol solution was prepared by mixing together 16.48 parts of A174, 10.99 parts of methanol, 1.49 parts of acetic acid, and 2.39 parts of deionized water. During mixing the silanol solution was kept in a temperature range of 20° C. to 30° C. Fumed silica (OX-50) (68.66 parts) (Degussa Corporation, Parsippany, N.J.) was charged to a V-blender and, with mixing, the silanol solution was added to the V-blender over the course of 30 minutes. The resulting dispersion was discharged from the V-blender into plastic-lined trays, dried for three hours and 45 minutes at 67° C., and then further dried for one hour and 15 minutes at 100° C. The resulting fine, free-flowing white powder was designated Filler C.

Filler D (Silane-Treated (3.5%) Silica Gel I): A174 (0.52 g) was added to a 250-ml beaker containing a stirred dispersion of Silica gel I (15 g) in deionized water (75 g, adjusted to pH=9.0-9.5 with ammonium hydroxide) and the resulting mixture stirred at room temperature for 14 hours. The resulting mixture was poured into a crystallization dish and dried at 125° C. in a forced air oven for approximately 3 hours to afford a white powder designated as Filler D.

Filler E (Silane-Treated (17.5%) Silica Gel I): Filler E was prepared in the same manner as Filler D, except that 2.63 g of A174 was used.

Filler F (Silane-Treated (3.5%) Silica Gel II): Filler F was prepared in the same manner as Filler D, except that Silica Gel II (20 g) was substituted for the Silica Gel I (15 g) and 0.7 g of A174 was used.

Filler G (Silane-Treated (7.0%) Precipitated Silica): Filler G was prepared in the same manner as Filler D, except that ACEMATT HK-450 Precipitated Silica (13.45 g, Degussa AG, Germany) was substituted for the Silica Gel I (15 g) and 1.15 g of A174 was used.

Filler H (Silane-Treated (3.5%) Precipitated Silica): Filler H was prepared in the same manner as Filler D, except that ACEMATT HK-460 Precipitated Silica (15.0 g, Degussa AG, Germany) was substituted for the Silica Gel I (15 g) and 0.53 g of A174 was used.

Example 1A

Filler of Silane-Treated Silica Clusters (Without Separate Calcining Step)

Silane-treated, nano-sized silica particles loosely aggregated as silica clusters were prepared in the form of a free-flowing dry powder according to the following procedure. Nalco 2329 silica sol (1.0 kg) was spray dried using a 91-cm Niro Spray Drier (Niro MOBILE MINOR Spray Drier, Columbia, Md.) at a 325° C. inlet temperature and a 120° C. outlet temperature. A 330-g sample of the resulting dry solid was added to a 5.5-liter jar mill and ball-milled for 16 hours to yield a white powder that was determined according to the Cluster Size Determination Test Method described herein to consist of silica clusters having an average size of 5 micrometers. Primary silica particles making up the silica clusters were assumed to be the same size as in the starting Nalco 2329 silica sol, i.e., having a nominal particle size of about 75 nanometers.

A 100-g sample of the white powder was thoroughly mixed with deionized water (300 g) by stirring for 2 minutes with a magnetic stir bar. The resulting homogeneous mixture was adjusted to a pH of 8.5 with ammonium hydroxide. A174 (3.5 g) was added, the contents thoroughly mixed for 120 minutes using a magnetic stir bar, and the resulting mixture adjusted to a final pH of 8.25. The mixture was then spray dried using a Buchi spray drier (Buchi/Brinkman Mini Spray Dryer, Model 190, Brinkmann Instruments, Inc., Westbury, N.Y.) at 200° C. inlet temperature and 85° C. outlet temperature. The resulting fine, free-flowing white powder was designated Example 1A Filler.

Example 1B

Filler of Silane-Treated Silica Clusters (with Separate Calcining Steps)

Silane-treated, nano-sized silica particles loosely aggregated as silica clusters were prepared as described for Example 1A, except that the dry solid resulting from the initial Niro Spray Drying was heat treated (calcined) at 550° C. for 3 hours before ball-milling and heat treated (post-calcined) at 550° C. for 6 hours after ball-milling. The white powder obtained following the post-calcined step was determined according to the Cluster Size Determination Test Method described herein to consist of silica clusters having an average size of 5 micrometers. Primary silica particles making up the silica clusters were assumed to be the same size as in the starting Nalco 2329 silica sol, i.e., having a nominal particle size of about 75 nanometers. The white powder was silane-treated and dried as described for Example 1A filler and the resulting fine, free-flowing white powder was designated Example 1B Filler.

Example 2 and Comparative Examples 1, 2 and 3

Paste Materials

Paste materials were made by thoroughly mixing Liquid Resin A with various combinations of Filler A (silica particles), Filler B (silica/zirconia clusters), Filler C (fumed silica), and Example 1A Filler (silica clusters) in the amounts and loading levels shown in Table 4. It was observed by probing the pastes with a dental instrument that Example 2 and Comparative Example 2 Pastes (both containing clusters of particles in the resin) were significantly less tacky (i.e., less sticky) than Comparative Example 1 Paste (containing essentially discrete silica particles and no silica clusters in the resin) and were significantly less tacky (i.e., less sticky) than Comparative Example 3 Paste (containing fumed silica in the resin). Selected paste samples were evaluated for SWD/Hardness (a measurement of stickiness) and subjected to TEM analysis. Transmission electron microscopy of the paste with the Example 1B filler showed particles including generally spherical clusters having an average size of approximately 5 micrometers.

Samples of the pastes were hardened according to standard procedures (as detailed in the Test Methods describe herein) and certain of the resulting hardened materials evaluated for visual opacity, polish retention, and mechanical strength.

TABLE 4

Composition of Paste Materials.

| Pastes | Resin A | | Ex. 1B Filler | | Filler A | | Filler B | | Filler C | | Filler Load |
|---|---|---|---|---|---|---|---|---|---|---|---|
| | g | % | g | % | g | % | g | % | g | % | % |
| Example 2 | 1.375 | 27.5 | 1.554 | 31.1 | 2.071 | 41.4 | — | — | — | — | 72.5 |
| Comp. Ex. 1 | 1.475 | 29.5 | — | — | 3.525 | 70.5 | — | — | — | — | 70.5 |
| Comp. Ex. 2 | 2.6 | 25.3 | — | — | 4.4 | 42.7 | 3.297 | 32.0 | — | — | 74.7 |
| Comp. Ex. 3 | 1.5 | 30.0 | — | — | 2.0 | 40.0 | — | — | 1.5 | 30.0 | 70.0 |

Examples 3–5 and Comparative Examples 4–5

Filled Materials

Composite materials were made by thoroughly mixing Liquid Resin A with various combinations of Filler A (silica particles) with Fillers D-H in the amounts and loading levels shown in Table 5. The rheology (stickiness, softness, and texture) of the resulting materials was determined by probing with a dental instrument and the observed results are reported in Table 5. It is seen from the results that the silica gel-containing materials (Examples 3–5) having a total filler loading of 61% were non-sticky, relatively soft, easy-to-handle pastes, whereas, the precipitated silica-containing materials (Comparative Examples 4 and 5) having total filler loadings of 55% and 60%, respectively, were very hard pastes or powders unsuitable for use as a dental paste. It is also noted that pastes preferably include at least about 55% total silica filler, more preferably at least about 60% total silica filler, to provide, upon curing, hardened materials having a useful balance of physical properties (e.g., low shrinkage, low wear rate) for dental applications.

TABLE 5

Composition and Rheological Properties of Filled Materials.

| Ingredient (g) | Ex. 3 | Ex. 4 | Ex. 5 | Comp. Ex. 4 | Comp. Ex. 5 |
|---|---|---|---|---|---|
| Resin A | 2 | 2 | 2 | 2.25 | 1.95 |
| Filler A | 1.742 | 1.742 | 1.742 | 1.571 | 1.714 |
| Filler D | 1.308 | | | | |
| Filler E | | 1.308 | | | |
| Filler F | | | 1.308 | | |
| Filler G | | | | 1.179 | |
| Filler H | | | | | 1.286 |
| Filler Loading % | 61 | 61 | 61 | 55 | 60 |
| Rheology of Resulting Filled Material | Non-sticky, soft paste | Non-sticky, soft paste | Non-sticky, soft paste | Powder | Partly very hard paste, partly powder |
| Usefulness as a dental restorative | Yes | Yes | Yes | No | No |

Evaluations and Results

Handling Properties: Handling properties of Example 2 Paste and Comparative Example 1B Paste were measured with a texture analyzer according to the Test Method described herein. The results in terms of Hardness, String Work Done (SWD), and the ratio of SWD/Hardness are reported in Table 6. The ratio of SWD/Hardness is an indication of paste stickiness with a lower number indicating a less-sticky paste. It can be concluded from the data shown in Table 6 that Example 2 Paste (with silica particles and silica clusters in Resin A) was significantly less sticky than Comparative Example 1 Paste (with essentially only silica particles in Resin A).

TABLE 6

Handling Properties - Indication of Paste Stickiness

| Paste Sample | Hardness | | String Work Done | | SWD/Hardness second |
|---|---|---|---|---|---|
| | gram (g) | SD | g-seconds | SD | |
| Example 2 | 972.5 | 25.5 | 157.8 | 4.0 | 0.162 |
| Comp. Example 1 | 10008.0 | 42.0 | 487.1 | 44.1 | 0.483 |

Visual Opacity: In order to quantitatively assess the translucency of the hardened materials obtained from the cured paste samples, measurements were made of direct light transmission (MacBeth Densitometer) and of Contrast Ratio according to the Test Methods described herein. Results for hardened materials from Example 2 Paste and Comparative Examples 1 and 2 Pastes are reported in Table 7. It can be concluded from the data shown in Table 7 that the hardened materials from Example 1 Paste (with silica particles and silica clusters) and Comparative Example 1 Paste (with essentially only silica particles) had low visual opacity (MacBeth light transmission values both less than 0.20 and Contrast Ratios both less than 30), whereas the hardened material from Comparative Example 2 Paste (with discrete silica particles and silica-zirconia clusters) had significantly higher visual opacity (MacBeth light transmission value of 0.50 and a Contrast Ratio of 62.3). The high degree of translucency of the hardened material from Example 2 Paste was surprising, considering the presence of a relatively high percentage (31% based on total resin) of larger-sized silica clusters (about 5 micrometers average size) in the material.

TABLE 7

Visual Opacity - Indication of Hardened Material Translucency

| Paste Sample (Cured to Provide Hardened Material) | MacBeth Value | Contrast Ratio |
|---|---|---|
| Example 2 | 0.14 | 23.61 |
| Comparative Example 1 | 0.18 | 27.15 |
| Comparative Example 2 | 0.50 | 62.3 |

Polish Retention: Polish retention of the hardened materials obtained from cured paste samples was evaluated according to the Test Method described herein. Results for hardened materials from Example 2 Paste and Comparative Example 1 Paste, along with the results of cured commercial dental pastes SILUX PLUS microfill composite (3M Company) and Z250-A2 hybrid (or macrofill) composite (3M Company) are reported in Table 8. It can be concluded from the data shown in Table 8 that the hardened materials from Example 2 Paste (with silica particles and silica clusters) and Comparative Example 1 Paste (with essentially only silica particles) both had very high polish retention after 500 brushings and both had significantly better polish retention than the Z250-A2 commercial material. Both the hardened Example 2 Paste and the hardened Comparative Example 1 Paste showed similar polish retention to the commercial SILUX PLUS microfill commercial material that represents the best of the polish-retention dental products currently available. The high degree of polish retention of the hardened material from Example 2 Paste was surprising, considering the presence of a relatively high percentage (31% based on total resin) of larger-sized silica clusters (about 5 micrometers average size) in the material.

TABLE 8

Polish Retention of Hardened Materials

| Paste Sample (Cured to Provide Hardened Material) | Number of Brushing | Average Gloss Units | Loss of Gloss % |
|---|---|---|---|
| Example 2 | 0 | 82.2 | — |
|  | 200 | 77.7 | 5.5 |
|  | 500 | 76.7 | 6.7 |
| Comp. Example 1 | 0 | 80.0 | — |
|  | 200 | 75.4 | 5.7 |
|  | 500 | 74.3 | 7.1 |
| SILUX PLUS | 0 | 84.1 | — |
|  | 200 | 80.5 | 4.3 |
|  | 500 | 75.4 | 10.3 |
| Z250-A2 | 0 | 82.1 | — |
|  | 200 | 65.0 | 20.9 |
|  | 500 | 60.3 | 60.3 |

Mechanical Strength: Mechanical strength of the hardened materials obtained from cured paste samples was determined by evaluation of diametral tensile strength (DTS) and compressive strength (CS) according to the Test Methods described herein. Results for hardened materials from Example 2 Paste, Comparative Example 1 Paste, and SILUX PLUS composite are reported in Table 9. It can be concluded from the data shown in Table 9 that all of the hardened materials tested had excellent mechanical strength properties.

TABLE 9

Diametral Tensile Strength and Compressive Strength

| Paste Sample (Cured to Provide Hardened Material) | DTS MPa | SD | CS MPa | SD |
|---|---|---|---|---|
| Example 2 | 76.55 | 5.18 | 444.14 | 31.24 |
| Comp. Example 1 | 75.17 | 8.62 | 431.03 | 27.86 |
| SILUX PLUS | 58.62 | 2.10 | 387.59 | 23.86 |

Bulk Density: The bulk density of the following three fillers were measured according to the Test Method described herein: Example 1 Filler (silica clusters), Filler C (silane-treated fumed silica OX 50), and organically treated fumed silica R7200 (Degussa Corporation). The results are provided in Table 10 and show that the bulk density of Example 1 filler including silica clusters is significantly higher than the bulk densities of the two fumed silica fillers.

TABLE 10

Bulk Densities of Fillers

| Filler Sample | Bulk Density (g/ml) |
|---|---|
| Example 1B (Silica Clusters) | 0.603 |
| Filler C (Silane-Treated Fumed Silica) | 0.332 |
| R7200 (Organically Treated Fumed Silica) | 0.237 |

Scanning electron microscopy (SEM, 3,000–10,000 magnification) of a dry powder of the Example 1B silica clusters showed generally spherical silica clusters having an average size of approximately 5 micrometers. In contrast, scanning electron microscopy (SEM, 3,000–10,000 magnification) of a dry powder of a fumed silica available under the trade designation OX-50 from DeGussa AG, (Hanau, Germany) (3,000–10,000 magnification) indicated that the fumed silica included fused, branched-chain, three-dimensional aggregates of particles having a nominal size of approximately 0.1–0.2 micrometers.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A dental paste comprising:
   a hardenable resin;
   a first filler dispersed in the resin, the first filler comprising aggregates of non-porous primary silica particles forming a porous, non-pyrogenic silica having a silane treated surface and being substantially free of heavy metals; and
   a second filler dispersed in the resin, the second filler comprising non-aggregated non-porous primary silica particles having a silane treated surface and having an average diameter of at most 200 nanometers, wherein the paste comprises at least 55% by weight of the combined first and second fillers.

2. The dental paste of claim 1 wherein the paste comprises at least 60% by weight of the combined first and second fillers.

3. The dental paste of claim 1 wherein the ratio of the first filler to the second filler is at least 1:4 by weight.

4. The dental paste of claim 1 wherein the ratio of the first filler to the second filler is at most 4:1 by weight.

5. The dental paste of claim 1 wherein the first filler comprises a silica gel.

6. The dental paste of claim 1 wherein the first filler comprises a silica cluster.

7. The dental paste of claim 1 wherein the porous, non-pyrogenic silica comprises aggregates of primary silica particles having an average particle size of about 5 nanometers to about 120 nanometers.

8. The dental paste of claim 7 wherein the aggregated silica has an average size of at least 1 micrometer.

9. The dental paste of claim 7 wherein the aggregated silica has an average size of about 1 micrometer to about 10 micrometers.

10. The dental paste of claim 7 wherein the aggregated silica has an average aspect ratio of at most 4:1.

11. The dental paste of claim 1 wherein the first filler has a bulk density of at least 0.4 g/cm.sup.3.

12. The dental paste of claim 1 wherein the hardenable resin is selected from the group consisting of acrylates, methacrylates, epoxies, and mixtures thereof.

13. The dental paste of claim 1 further comprising an initiator.

14. The dental paste of claim 1 wherein the paste is substantially non-sticky.

15. The dental paste of claim 1 having a String Work Done/Hardness value of at most 0.5.

16. The dental paste of claim 1 wherein the paste forms a material selected from the group consisting of dental restoratives, dental adhesives, casting materials, dental cements, dental sealants, and dental coatings.

17. The dental paste of claim 1 wherein the paste, upon hardening, has one or more properties selected from the group consisting of: a contrast ratio of at most 50, a MacBeth value of at most 0.4, a volumetric shrinkage of at most 4%, a diametral tensile strength of at least 15 MPa, a compressive strength of at least 35 MPa, and a loss in polish of at most 3% after 500 brushes in a polish retention test.

18. A method of preparing a dental paste comprising:
dispersing in a hardenable resin a first filler comprising aggregates of substantially non-porous primary silica particles forming a porous, non-pyrogenic silica having a silane treated surface and being substantially free of heavy metals; and
dispersing in the hardenable resin a second filler comprising non-aggregated substantially non-porous primary silica particles having a silane treated surface and having an average particle size of at most 200 nanometers to form a paste, wherein the paste comprises at least 55% by weight of the combined first and second fillers.

19. A dental article comprising:
a hardened resin;
a first filler dispersed in the hardened resin, the first filler comprising aggregates of substantially non-porous primary silica particles forming porous, non-pyrogenic silica having a silane treated surface and being substantially free of heavy metals;
and a second filler dispersed in the hardened resin, the second filler comprising non-aggregated substantially non-porous primary silica particles having a silane treated surface and having an average particle size of at most 200 nanometers, wherein the article comprises at least 55% by weight of the combined first and second fillers.

20. The dental article of claim 19 wherein the article is selected from the group consisting of dental mill blanks, dental prostheses, orthodontic devices, artificial crowns, anterior fillings, posterior fillings, and cavity liners.

21. The dental article of claim 19 having one or more properties selected from the group consisting of: a contrast ratio of at most 50, a MacBeth value of at most 0.4, a diametral tensile strength of at least 15 MPa, a compressive strength of at least 35 MPa, and a loss in polish of at most 30% after 500 brushes in a polish retention test.

22. A method of preparing a dental article comprising:
dispersing a first filler in a hardenable resin, the first filler comprising aggregates of substantially non-porous primary silica particles forming porous, non-pyrogenic silica having a silane treated surface and being substantially free of heavy metals;
dispersing a second filler in the resin, the second filler comprising non-aggregated substantially non-porous primary silica particles having a silane treated surface and having an average particle size of at most 200 nanometers to form a paste,
wherein the paste comprises at least 55% by weight of the combined first and second fillers; and hardening the paste to fabricate a dental article selected from the group consisting of dental mill blanks, dental prostheses, orthodontic devices, artificial crowns, anterior fillings, posterior fillings, and cavity liners.

23. The method of claim 22 further comprising changing the topography of the paste before hardening the paste.

* * * * *

UNITED STATES PATENT AND TRADEMARK OFFICE
CERTIFICATE OF CORRECTION

PATENT NO. : 7,393,882 B2  Page 1 of 1
APPLICATION NO. : 10/353505
DATED : July 1, 2008
INVENTOR(S) : Dong Wu It is certified that error appears in the above-identified patent and that said Letters Patent is hereby corrected as shown below:

<u>Title Page, Item (56) on Page 3, in Column 1, under (Other Publications)</u>
Line 5, delete "311-338." and insert -- 311-338 (1958). --, therefor.

<u>Title Page, Item (56) on Page 3, in Column 2, under (Other Publications)</u>
Line 43, delete "(no date available)." and insert -- (2002). --, therefor.
Line 47, delete "Commericial" and insert -- Commercial --, therefor.

<u>Column 26</u>
Line 26, delete "10008.0" and insert -- 1008.0 --, therefor.

<u>Column 27</u>
Line 24, delete "Brushing" and insert -- Brushings --, therefor.

<u>Column 29</u>
Line 22, in Claim 17, delete "3%" and insert -- 30% --, therefor.

Signed and Sealed this

Thirtieth Day of September, 2008

JON W. DUDAS
*Director of the United States Patent and Trademark Office*